(12) United States Patent  
Anukhin et al.

(10) Patent No.: US 8,998,945 B2
(45) Date of Patent: Apr. 7, 2015

(54) METHODS AND APPARATUS FOR FILTERING A BODY LUMEN

(75) Inventors: Boris Anukhin, San Jose, CA (US); David Mackiewicz, Scotts Valley, CA (US); Michael L. Green, Pleasanton, CA (US); Sanjay Shrivastava, Irvine, CA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 549 days.

(21) Appl. No.: 13/131,254

(22) PCT Filed: Dec. 16, 2009

(86) PCT No.: PCT/US2009/068291
§ 371 (c)(1),
(2), (4) Date: Dec. 14, 2011

(87) PCT Pub. No.: WO2010/077966
PCT Pub. Date: Jul. 8, 2010

(65) Prior Publication Data
US 2012/0083822 A1      Apr. 5, 2012

Related U.S. Application Data

(60) Provisional application No. 61/138,461, filed on Dec. 17, 2008.

(51) Int. Cl.
*A61M 29/00*  (2006.01)
*A61F 2/01*  (2006.01)
*A61F 2/88*  (2006.01)

(52) U.S. Cl.
CPC ... *A61F 2/01* (2013.01); *A61F 2/88* (2013.01); *A61F 2002/011* (2013.01);

(Continued)

(58) Field of Classification Search
CPC ..... A61F 2/01; A61F 2/02; A61F 2230/0069; A61F 2/013
USPC ......... 606/200, 198, 159, 110, 113, 114, 127; 623/1.36, 1.18, 1.13
See application file for complete search history.

(56) References Cited

U.S. PATENT DOCUMENTS 5,466,242 A * 11/1995 Mori .............................. 606/198
5,797,953 A *  8/1998 Tekulve ........................ 606/200

(Continued)

FOREIGN PATENT DOCUMENTS

WO   WO83/00997   3/1983
WO   WO03/022325  3/2003

(Continued)

OTHER PUBLICATIONS

U.S. Appl. No. 61/138,461, filed Dec. 17, 2008, Anukhin et al.

*Primary Examiner* — Katrina Stransky
(74) *Attorney, Agent, or Firm* — Workman Nydegger; Jonathan D. Feuchtwang

(57) ABSTRACT

An implantable lumen filter is described. The filter may include a body formed from an elongate member. The body may include loops encircling an axis extending along the length of the body. The body may be sized to be implanted into a body lumen. The body may be capable of transitioning from a collapsed state to a deployed state. The filter may include a first group of a plurality of members positioned around at least one loop of said body. At least a portion of the plurality of members may be oriented towards the axis. The plurality of members may be arranged to capture and/or lyse particulates of a selected size and/or to inhibit the particulates from passing through the body. Methods of making, deploying, and retrieving the same are described.

45 Claims, 18 Drawing Sheets

(52) U.S. Cl.
CPC .. *A61F 2002/016* (2013.01); *A61F 2230/0006* (2013.01); *A61F 2230/005* (2013.01); *A61F 2230/0069* (2013.01); *A61F 2230/0091* (2013.01)

(56) References Cited

U.S. PATENT DOCUMENTS

| | | | | |
|---|---|---|---|---|
| 5,833,699 | A | * | 11/1998 | Chuter .......................... 623/1.15 |
| 6,059,825 | A | * | 5/2000 | Hobbs et al. .................. 623/1.18 |
| 6,117,157 | A | * | 9/2000 | Tekulve ........................ 606/200 |
| 6,425,909 | B1 | * | 7/2002 | Dieck et al. ................... 606/200 |
| 6,468,290 | B1 | * | 10/2002 | Weldon et al. ................ 606/200 |
| 6,485,497 | B2 | * | 11/2002 | Wensel et al. ................. 606/159 |
| 6,986,784 | B1 | * | 1/2006 | Weiser et al. .................. 623/1.1 |
| 7,862,608 | B2 | * | 1/2011 | Hogendijk et al. .......... 623/1.22 |
| 2004/0186512 | A1 | * | 9/2004 | Bruckheimer et al. ....... 606/200 |
| 2005/0004598 | A1 | * | 1/2005 | White et al. .................. 606/200 |
| 2006/0036279 | A1 | | 2/2006 | Eidenschink et al. |
| 2007/0093744 | A1 | * | 4/2007 | Elmaleh ......................... 604/22 |
| 2007/0173885 | A1 | | 7/2007 | Cartier et al. |
| 2007/0208371 | A1 | | 9/2007 | French et al. |

FOREIGN PATENT DOCUMENTS

| | | |
|---|---|---|
| WO | WO2005/094283 | 10/2005 |
| WO | WO2007/061927 | 5/2007 |
| WO | WO2008/010197 | 1/2008 |
| WO | WO2010/077966 | 7/2010 |

* cited by examiner

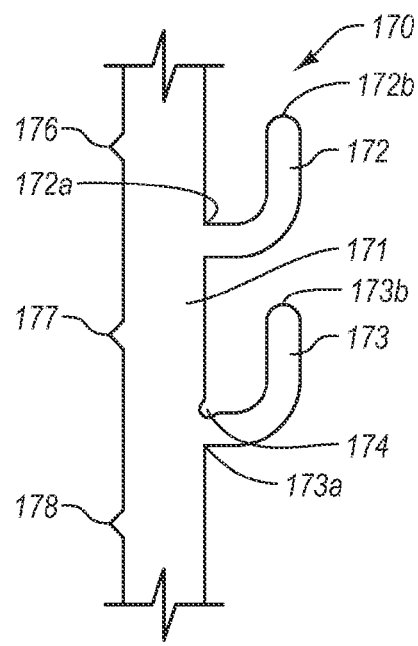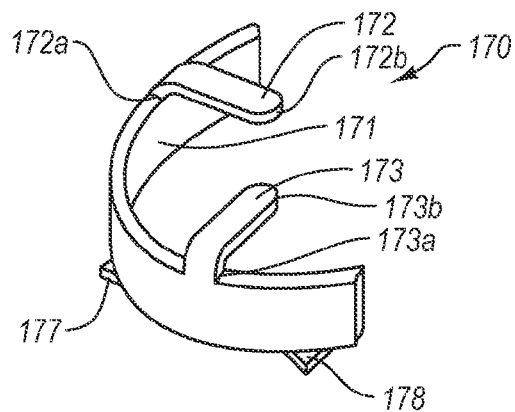
Fig. 5A
Fig. 5B
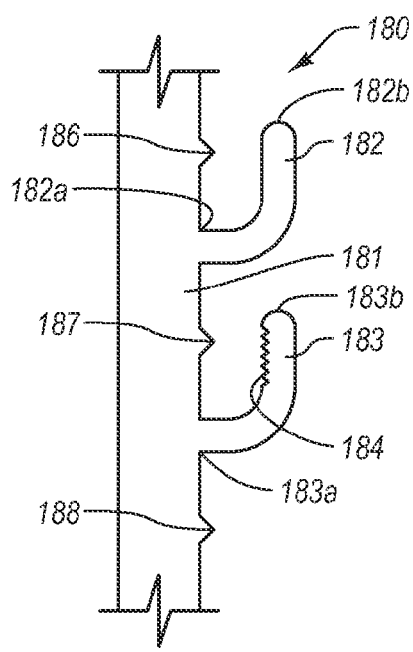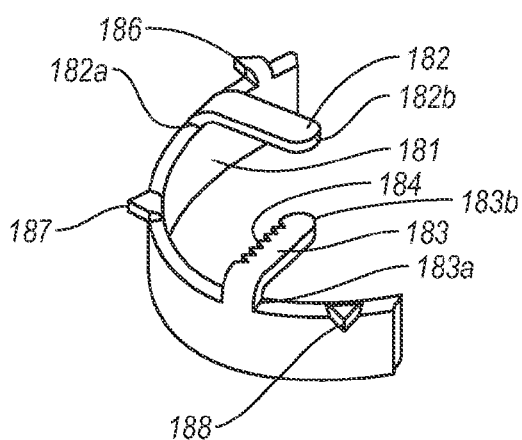
Fig. 6A
Fig. 6B

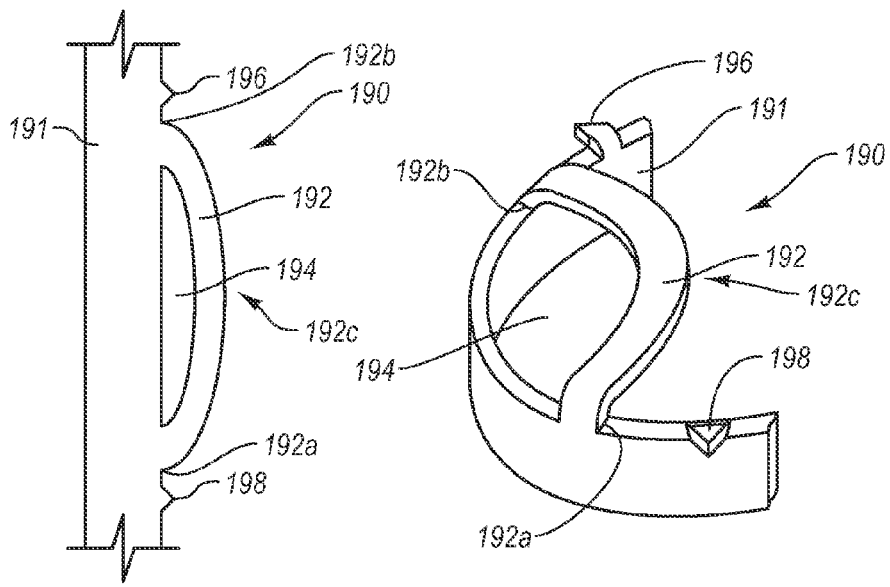
Fig. 7A
Fig. 7B
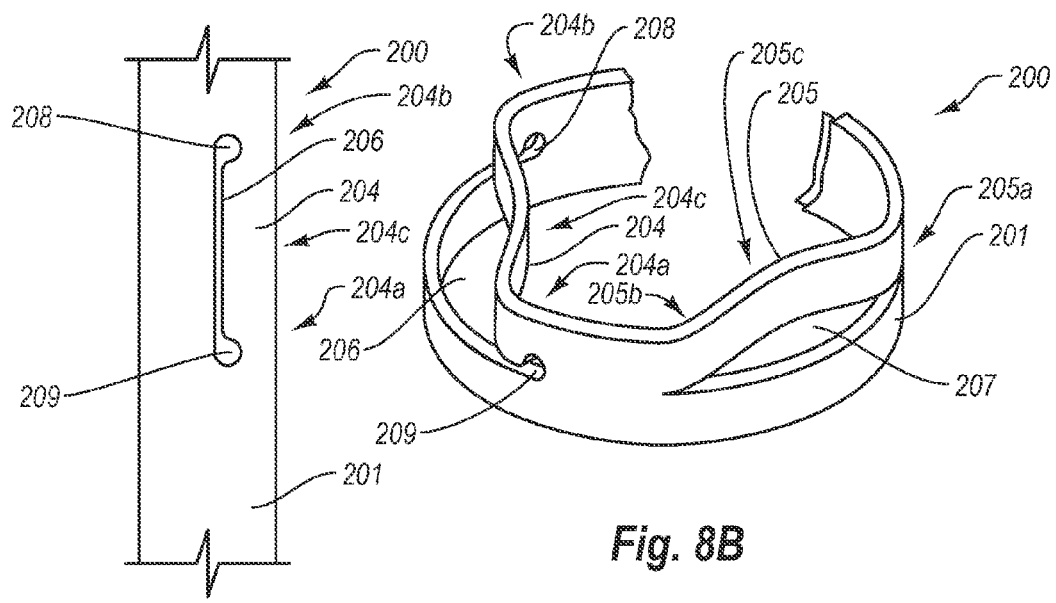
Fig. 8A
Fig. 8B

*Fig. 25D"*

METHODS AND APPARATUS FOR FILTERING A BODY LUMEN

CROSS-REFERENCE TO RELATED APPLICATIONS

This patent application claims the benefit of and priority to U.S. Provisional Patent Application having Ser. No. 61/138,461, filed on Dec. 17, 2008, the disclosure of which is incorporated herein by reference in its entirety.

FIELD OF THE INVENTION

The present invention relates generally to medical devices. More particularly the present invention relates to methods and apparatus for filtering a body lumen.

BACKGROUND OF THE INVENTION

Vein thrombosis is a medical condition wherein a blood clot, or thrombus, has formed inside a vein. Such a clot often develops in the calves, legs, or lower abdomen, but can also affect other vasculature in the body. The clot may partially or completely block bodily fluid flow and may break off and travel through the bloodstream (as an embolus). Commonly, clots are caused by a pooling of blood in the vein, often when an individual is bed-ridden for an abnormally long duration of time, for example, when resting following surgery or suffering from a debilitating illness, such as a heart attack or traumatic injury. However, there are other situations that may cause the formation of a blood clot.

Vein thrombosis is a serious problem because of the danger that the clot may break off and travel through the bloodstream to the lungs, causing a pulmonary embolism. This is similar to a blockage of the blood supply to the lungs that causes severe hypoxia and cardiac failure, which frequently result in death. For many patients, anti-coagulant drug therapies may be sufficient to dissipate the clots. For example, patients may be treated with anticoagulants such as heparin and with thrombolytic agents such as streptokinase.

Unfortunately, some patients may not respond to such drug therapy or may not tolerate such therapy. Also, there may be other reasons why an anticoagulant is not desirable. For example, patients may have an acute sensitivity to heparin or may suffer from prolonged internal and/or external bleeding as a result of such drug therapies. Also, such drug therapies simply may be ineffective in preventing recurrent pulmonary emboli. In such circumstances, surgical procedures may be necessary to reduce the likelihood of pulmonary emboli. Mechanical interruption of the inferior vena cava typically presents an effective method of preventing of pulmonary embolisms.

Vena cava filters are devices which are implanted in the inferior vena cava, providing a mechanical barrier to undesirable particulates. The filters may be used to filter peripheral venous blood clots and/or other particulates, which if remaining in the blood stream can migrate in the pulmonary artery or one of its branches and cause harm. However, vena cava filters may be improved.

Therefore, methods and apparatus for filtering a body lumen may be useful.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIGS. 5A-5B are partial cutaway views of an example of an implantable lumen filter.

FIGS. 6A-6B are partial cutaway views of another example of an implantable lumen filter.

FIGS. 7A-7B are partial cutaway views of a further example of an implantable lumen filter.

FIGS. 8A-8B are partial cutaway views of a still further example of an implantable lumen filter.

Figure 1:
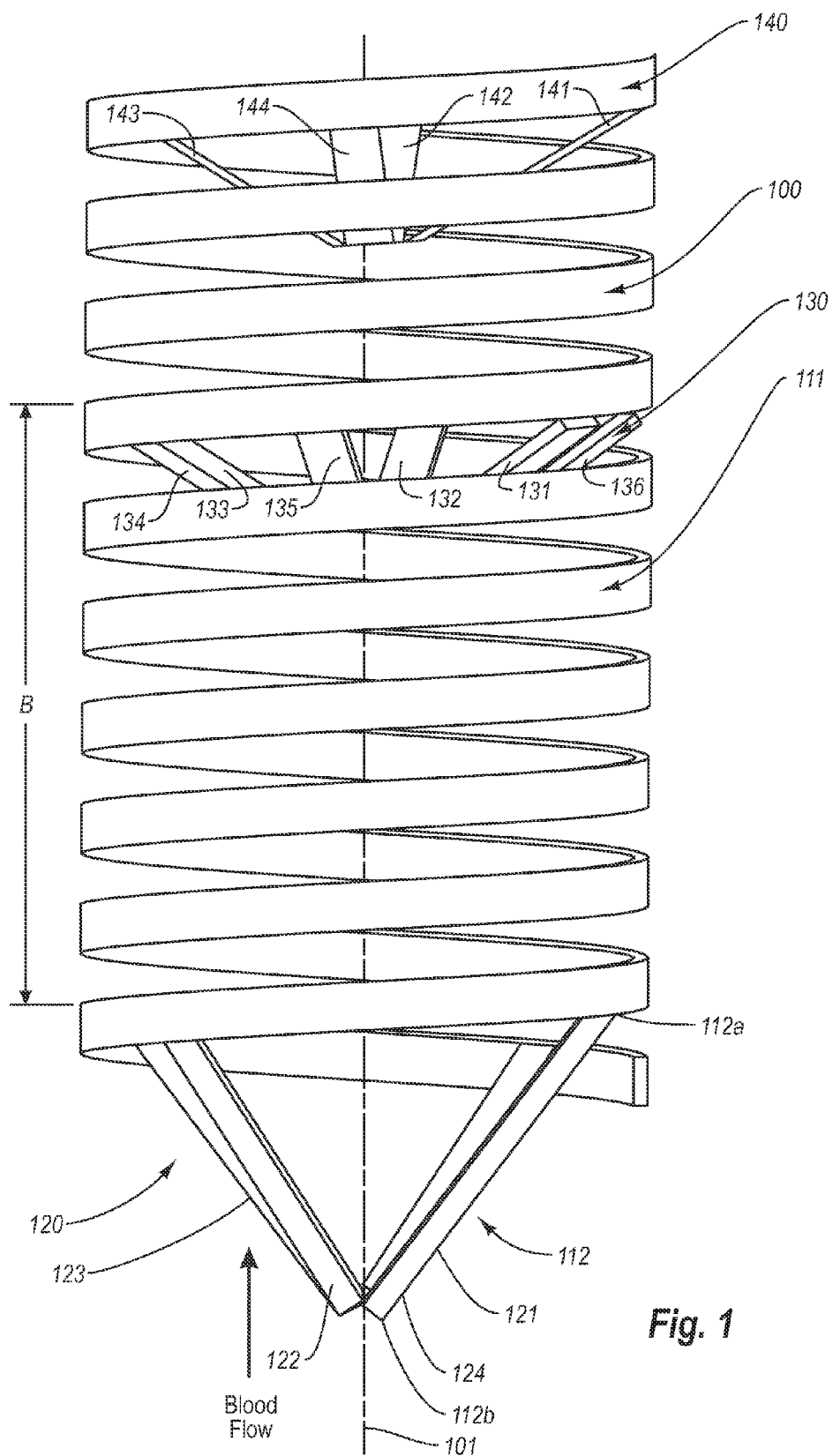
FIG. 1 is a side view of an implantable lumen filter.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

The configurations described herein extend generally to implantable lumen filters, retrieving mechanisms, methods of manufacturing the same, and methods for filtering a body lumen. By way of example only, a body lumen may include a blood vessel. Filtering of the body lumen may be performed by implantable lumen filters. For instance, configurations of implantable lumen filters (e.g. including vena cava and/or other lumen filters), are described. Components of implantable filters also are described.

Some implantable lumen filters may be designed to capture, inhibit, and/or lyse particulates of a particular size within the lumen. Many implantable lumen filters may be generally tapered from a distal end toward a proximal end. For example, implantable lumen filters may be generally cone shaped. As a result of their shape, many implantable lumen filters may direct particulates towards and capture, inhibit, and/or lyse the particulates within a central portion of the lumen. As particulates collect within the filter near the center of the lumen, flow within the lumen, such as bodily fluid flow, is disrupted and/or reduced. This can lead to an occlusion thereby reducing the usable lifespan of the filter and potentially causing harm to a patient.

Example implantable lumen filters described herein may be configured to direct particulates within a lumen radially outwardly and/or to collect particulates proximate an inner wall of the lumen. By so doing, some example implantable lumen filters described herein can reduce or eliminate obstructions within the central portion of the lumen. Some implantable lumen filters may provide enhanced durability. As a result, these implantable lumen filters may have longer usable lifespans and/or enhanced safety characteristics.

Some embodiments of implantable lumen filters described herein may have a generally spiral or helical shape. Implantable lumen filters may be used in various vasculatures. For example, embodiments of implantable lumen filters may be configured for use in the vena cava.

During retrieval, a second filter can be temporarily deployed above the filter that is being retrieved to prevent breakage of earlier captured particulates, such as emboli. Multiple filters may be used along a length of a body lumen during retrieval or otherwise. The use of multiple filters may reduce the likelihood that a particulate may harm a patient. For example, when one filter fills, others may be positioned downstream to capture, inhibit, and/or lyse additional particulates.

The spiral filters can be deployed and recovered from a body lumen, such as the vena cava through various access sites. For example, a spiral filter may be deployed and/or removed through a femoral approach, a brachial approach, or other access sites.

The example implantable lumen filters described herein may be manufactured from any suitable material. For example, an implantable lumen filter may be made from a biocompatible shaped memory material (SMM). For example, the SMM can be shaped in a manner that allows for a pre-deployed configuration while within a delivery device, but can automatically retain the memory shape of the filter once deployed from the delivery device and into the body lumen. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have an initial shape that can then be configured into a memory shape by heating the SMA and conforming the SMA into the desired memory shape. After the SMA is cooled, the desired memory shape can be retained. This allows for the SMA to be bent, straightened, twisted, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture. This can be used to tune the filter so that it reverts to the memory shape within the body lumen when deployed at body temperature and when being released from the delivery device.

For instance, the primary material of a filter can be of a NiTi alloy that forms superelastic nitinol. In the present case, nitinol materials can be trained to remember a certain shape, retained within the delivery device, and then deployed from the delivery device so that the filter expands within the body lumen. Also, additional materials can be added to the nitinol depending on the desired characteristic. The alloy may be utilized having linear elastic properties or non-linear elastic properties.

An SMP is a shape-shifting plastic that can be fashioned into a filter in accordance with the present disclosure. Also, it can be beneficial to include at least one layer of an SMA and at least one layer of an SMP to form a multilayered body; however, any appropriate combination of materials can be used to form a filter. When an SMP encounters a temperature above the lowest melting point of the individual polymers, the blend makes a transition to a rubbery state. The elastic modulus can change more than two orders of magnitude across the transition temperature (Ttr). As such, an SMP can formed into a desired shape of a filter by heating it above the Ttr, fixing the SMP into the new shape, and cooling the material below Ttr. The SMP can then be arranged into a temporary shape by force and then resume the memory shape once the force has been applied. Examples of SMPs include, but are not limited to, biodegradable polymers, such as oligo($\epsilon$-caprolactone) diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present disclosure.

A filter body having at least one layer made of an SMM or suitable superelastic material, and other suitable layers can be compressed or restrained in its delivery configuration within the delivery device, and then deployed into the body lumen so that it transforms to the trained shape. Thus, providing an implantable lumen filter that may transition from a compressed state toward a deployed shape.

Also, the filter can be comprised of a variety of known suitable deformable materials, including stainless steel, silver, platinum, tantalum, palladium, nickel, titanium, nitinol, nitinol having tertiary materials, niobium-tantalum alloy optionally doped with a tertiary material cobalt-chromium alloys, or other biocompatible materials. Such biocompatible materials can include a suitable biocompatible polymer in addition to or in place of a suitable metal. The polymeric clip can include biodegradable or bioabsorbable materials, which can be either plastically deformable or capable of being set in the deployed configuration.

In one embodiment, the filter may be made from a superelastic alloy such as nickel-titanium or nitinol, and includes a ternary element selected from the group of chemical elements such as iridium, platinum, gold, rhenium, tungsten, palladium, rhodium, tantalum, silver, ruthenium, hafnium, other radiopaque materials, alloys thereof, or combinations thereof. The added ternary element may improve the radiopacity of the nitinol filter. The nitinol filter may have improved radiopacity yet retain its superelastic and shape memory behavior and further may maintain a thin body thickness for high flexibility. For instance, the filter according to the present disclosure may have 42.8 atomic percent nickel, 49.7 atomic percent titanium, and 7.5 atomic percent platinum.

These materials may include at least one beneficial agent incorporated into the material and/or coated over at least a portion of the material. The beneficial agents may be applied to implantable lumen filters that have been coated with a polymeric compound. Incorporation of the compound or drug into the polymeric coating of the implantable lumen filter can be carried out by dipping the polymer-coated implantable lumen filter into a solution containing the compound or drug for a sufficient period of time (such as, for example, five minutes) and then drying the coated implantable lumen filter, such as by way of air drying for a sufficient period of time (such as, for example, 30 minutes). The polymer-coated implantable lumen filter containing the beneficial agent may then be delivered to a body vessel.

The pharmacologic agents that can be effective in preventing restenosis can be classified into the categories of anti-proliferative agents, anti-platelet agents, anti-inflammatory agents, anti-thrombotic agents, and thrombolytic agents. Anti-proliferative agents may include, for example, crystalline rapamycin. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or αvβ3, antibodies that block binding to gpIIaIIIb or αvβ3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL 4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered is factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

One or more immunosuppressant agents may be used. Immunosuppressant agents may include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAM tacrolimus (also known as FK-506), sirolimus and RAPAMUNE®, leflunomide (also known as HWA-486), glucocorticoids, such as prednisolone and its derivatives, antibody therapies such as orthoclone (OKT3) and Zenapax®, and antithymyocyte globulins, such as thymoglobulins. In addition, a crystalline rapamycin analog, A-94507, SDZ RAD (a.k.a. Everolimus), and/or other immunosuppressants.

Referring now to the figures, FIG. 1 illustrates an example of an implantable lumen filter 100. The filter 100 may incorporate any of the features and/or components of any of the filters described herein. In some embodiments, the filter 100 can be formed into a spiral, helical, other winding shape, or combinations thereof. For instance, a wire, ribbon, plate, other shape, or combinations thereof may be coiled (i.e. wound) to from a body 111 and/or other filter components in a desired configuration, such as the helical configuration shown in FIG. 1. In another example, the body 111 and/or other components of the filter 100 can be formed from a tube that is formed in a desired configuration using forming techniques such as using laser cutting, photolithography, chemical etching, EDM, milling, hydro-cutting, other forming techniques, or combinations thereof.

The body 111 may include loops (i.e. windings) that may be oriented about an axis 101 extending along the length of the body. As shown in FIG. 1, the axis 101 may be generally straight. In other embodiments, the axis 101 may vary along the length of the filter 100. For example, the axis 101 may be curved or otherwise shaped. The length generally is defined as the length from end to end of the helical shape that forms the body of the filter; the width being defined as the cut breadth that forms each loop of the spiral configuration; and the thickness being defined as the depth of the material used to form the filter. The loops of the body 111 may be spaced apart from each other, as shown in FIG. 1. The spacing may vary or be the same from loop to loop.

The body 111 is sized to be implanted into a body lumen. The outer diameter of the body 111 is dimensioned to fit within a body lumen depending on the size of the lumen. The diameter, for example, can be between about 0.5 mm to about 70 mm. The length of the filter can be sized to meet various requirements, such as filtration, spacing, other requirements, or combinations of the same. For example, the length can be sized between about 25 mm and 50 mm. The thickness of the material may be based on the material selection and properties and can be sized, for example, between 0.006 cm and about 0.009 cm. Other sizes may be selected based on the diameter needed to fit inside the body lumen, the amount of filtration needed, the size of the material used to form the filter, other considerations, or combinations thereof.

Impeding members 112 (referred to generally as 112 and individually as 121, 122, 123, 124, 131, 132, 133, 134, 135, 136, 141, 142, 143, 144) may be formed as part of or attached to the filter body 111 and may include a first end 112*a* and/or a second end 112*b*. The impeding members 112 may facilitate the direction of particulates away from the center of the filter 100, which can potentially obstruct bodily fluid flow. In embodiments where the impeding members 112 are attached to the filter 100, the first end 112*a* can be attached to the body 111 by welding, soldering, adhering, other attaching methods, or combinations thereof. Alternatively and/or in addition, the first end 112*a* may be integrally formed with the body 111. The impeding members 112 may extend from the first end 112*a* toward the second end 112*b*.

The members 112 can be oriented with respect to the flow of bodily fluid through the body lumen. In the embodiment shown in FIG. 1, some members 112 (121, 122, 123, 124) are shown oriented at an angle A from the axis 101. Angle A can be arranged between about 10 degrees and about 80 degrees from the central axis 101 of the filter body 111 near the impeding member 112. The impeding member 112 may be generally oriented toward the bodily fluid flow so particulates traveling in the flow may be contacted by the second end 112*b* of the impeding member 112.

The filter 100 can include one or more members 112 distributed around the filter body 111. The members 112 can be arranged at any point around the body 111. The members 112 can be evenly and/or unevenly distributed around the body 111. For instance, the members 112 may be positioned at regular intervals, such as for example every ninety degrees about the body 111. In another example, the members 112 may be positioned at irregular intervals (i.e. at least two members being separated by fifteen degrees and at least two other members being separated by forty five degrees).

The impeding members 112 may be arranged in groups. The groups of members 112 can be arranged around a loop of the body 111 and can be configured to extend at least a portion of the member 112 towards an axis 101 running along the length of the body. The members 112 may be arranged to capture, inhibit, and/or lyse particulates and be dimensioned to allow blood components smaller than the selected size to pass between the members. In the present embodiment, the filter 100 may include three groups 120, 130, 140. In other embodiments more or fewer groups may be used.

The groups 120, 130, 140 may have various configurations. The groups 120, 130, 140 may include at least one member 112. The members 112 in each group 120, 130, 140 may vary in size, length, orientation, material, other characteristics, or combinations thereof from the members 112 in the group 120, 130, 140 and/or the members 112 in other groups 120, 130, 140. The groups 120, 130, 140 may have the same number of members 112, different numbers of members 112, or combinations thereof. For example, the first group 120 may include four members 121, 122, 123, 124, the second group 130 may include six members 131, 132, 133, 134, 135, 136, and the third group 140 may include four members 141, 142, 143, 144.

In the present embodiment, the first group 120 may include four members 121, 122, 123, 124 that may be placed around a loop of the body 111 near one end of the filter 100. The four members 121, 122, 123, 124 can be spaced around the body 111 at about 90 degree spacing radiating towards the central axis 101 of the filter 111 in a generally circular fashion. The first group 120 is angled against the bodily fluid flow through the body lumen as discussed above. The first group 120 can be angled at a steep incline to direct the particulates away from the central axis 101 and towards the body 111 of the filter 100. The steep angle, for example, may range between about 10 degrees and about 45 degrees from the central axis 101 of the filter 100. For instance the angle can be set at about 30 degrees.

A second group 130 may include six members 131, 132, 133, 134, 135, 136. The second group 130 can be offset a distance B from the first group 120. The distance B may be a longitudinal distance. The distance B, for example, can be about ⅔ of the total length of the body 111. The second group 130 may be placed around a loop of the body 111 and spaced about 60 degrees apart from each other radiating generally towards the central axis 101 of the filter 100. The second group 130, in the present embodiment, may contain more members 131, 132, 133, 134, 135, 136 than the first group 120. In other embodiments, the second group 130 may contain the same number of or fewer members 112 than the first group 120. The members 131, 132, 133, 134, 135, 136 may be arranged to capture, inhibit, and/or lyse particulates in the body lumen. The second group 130, in the present embodiment, may be configured to have a more gradual angle, such as an angle between about 45 degrees and about 85 degrees from the central axis 101 of the filter 100. A more gradual angle may facilitate capturing, inhibiting, and/or lysing the particulates. For instance the angle can be set at about 60 degrees.

In the present embodiment, the third group 140 may include four members 141, 142, 143, 144. In other embodiments, the third group 140 may contain the same number of or fewer members 112 than the first and/or second group 120, 130. The third group 140 may be placed around a loop of the body 111 near an end of the filter 100 opposite the first group 120. The four members 141, 142, 143, 144 can be spaced around the body 111 at about 90 degree spacing radiating towards the central axis 101 of the filter 100 in a circular fashion. The third group 140 may be angled against the bodily fluid flow through the body lumen as discussed above. The third group 140 may be angled at a gradual incline to further capture, inhibit, and/or lyse particulates in the filter 100. The gradual angle, for example, may range between about 45 degrees and about 85 degrees from the central axis 101 of the filter 100. For instance the angle can be set at about 45 degrees.

The impeding members 112 may be angled to facilitate the direction of particulates away from the central axis 101 to prevent obstruction of the bodily fluid flow. Members 112 that are non-perpendicular to the central axis 101 may capture, inhibit, and/or lyse particulates near the central axis 101 of the filter 100 and may move particulates toward the body 111 and away from the central axis 101.

Figure 2:
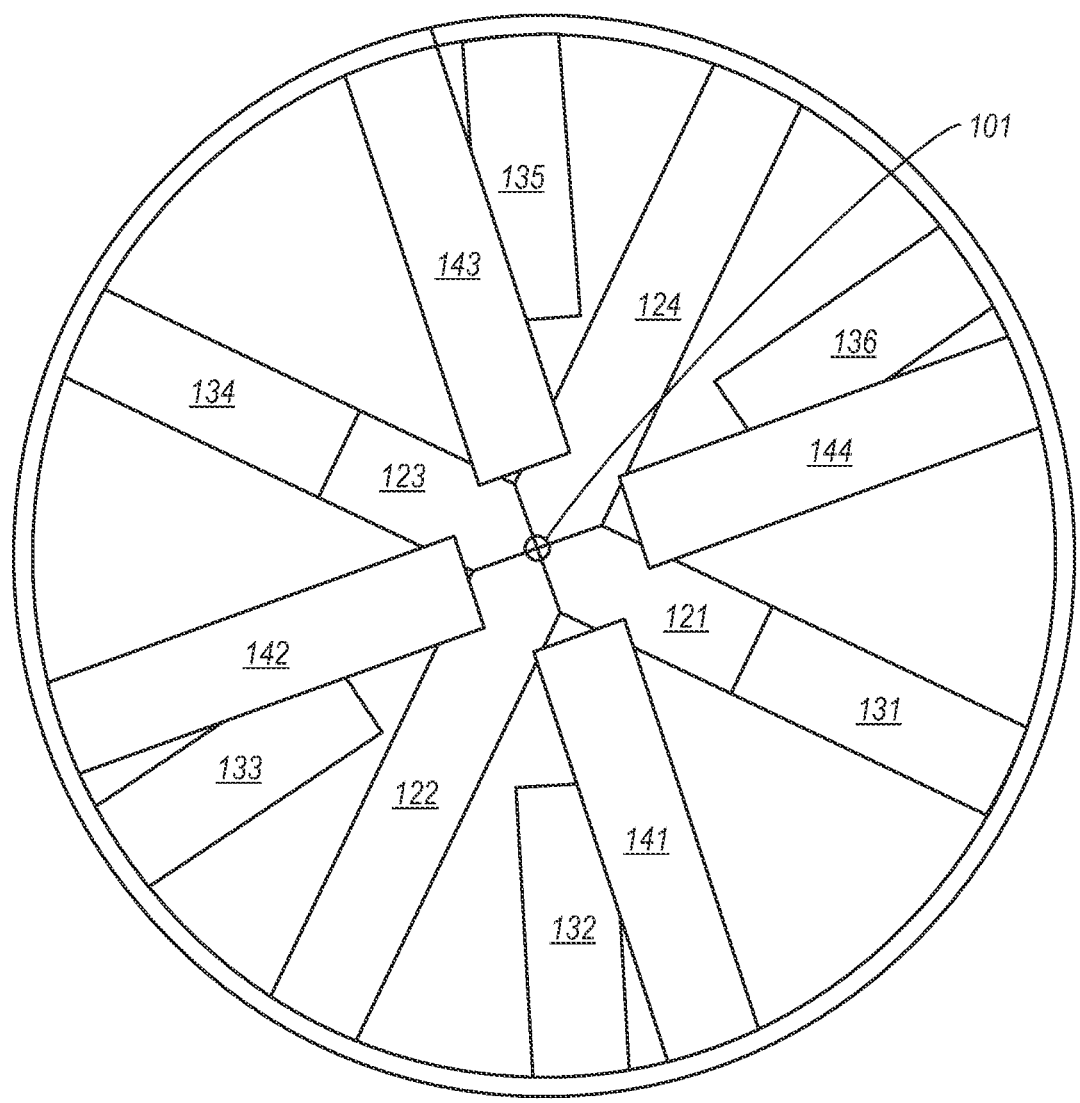
FIG. 2 is an end view of the implantable lumen filter of FIG. 1.

FIG. 2 is an end view of the implantable lumen filter 100 illustrated in FIG. 1. The impeding members 112 may be staggered to capture, inhibit, and/or lyse particulates that may be present in a bodily fluid flow through a body lumen. The members 112 in the first group 120 may be arranged with about 90 degree spacing and/or may extend toward the central axis 101 of the filter 100. The members 112 of the second group 130 may be arranged with about 60 degree spacing and/or extending over half the distance toward the central axis 101 of the filter 100. The members 112 of the third group 140 may be arranged with about 90 degree spacing and/or extending about the total distance toward the central axis 101 of the filter 100, such as ⅚ of the total distance. The third group 140 can be offset from the first group 120 by about 45 degrees to stagger the members 112 through the filter 100. As discussed above, the members 112 of the various groups 120, 130, 140 may vary in size, length, orientation, material, other characteristics, or combinations thereof from the members 112 in the group 120, 130, 140 and/or the members 112 in other groups 120, 130, 140.

Although the implantable lumen filter 100 illustrated in FIGS. 1 and 2 is an example of one embodiment, other configurations can be implemented. For example, the groups 120, 130, 140 can include more or less members 112, the members 112 can have varying positioning, such as angles or tilts, and can be arranged around the filter 100 with varying spacing, and the filter 100 can include more or less groups 120, 130, 140 than illustrated, other variations, or combinations thereof. A filter material can also be attached to and/or span across the impeding members 112 to add a further layer of filtration to capture, inhibit, and/or lyse finer particulates. The material may include a urethane, rubber, other material, or combinations thereof and/or holes formed by laser cutting, perforation, other forming techniques, or combinations thereof, which may be adhered to the impeding members 112 to form a filtration wall within the filter body 111. Various beneficial agents may be applied to the filter material or the body 111 of the filter 100 to facilitate lysing of particulates and/or to facilitate a reduction in body lumen growth around the filter 100 while in place for long periods of time.

A plurality of protruding engaging portions may be formed with or attached to the filter. If the engaging portions are attached to the filter, they can be attached by welding, adhering, or other techniques to affix a component to the body 111. The engaging portions may be configured to hold the filter 100 in place in a body lumen. The engaging portions can be strategically placed around the body 111 to increase the stability of the filter 100. The engaging portions may engage an inner surface of a body lumen. The engaging portions can include a tissue piercing portion that is configured to pierce a portion of the inner surface of the body lumen and/or a tissue engaging portion that is configured to engage but not pierce the inner surface of the body lumen.

Figure 3:
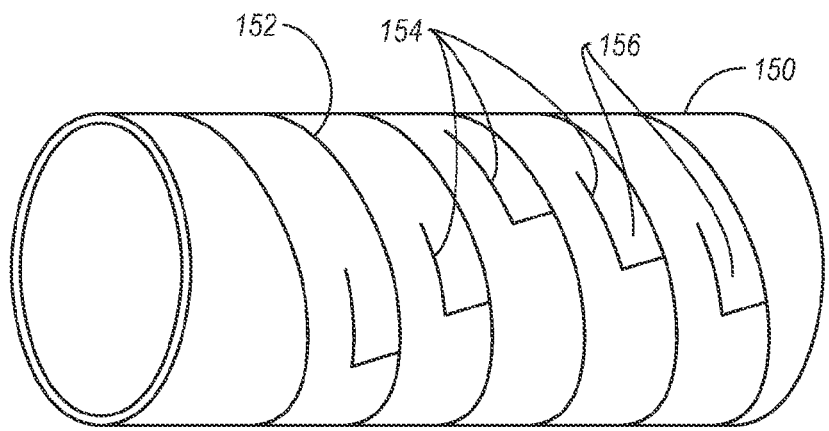
FIG. 3 illustrates an embodiment of an implantable lumen filter formed from a tube structure.
Figure 4:
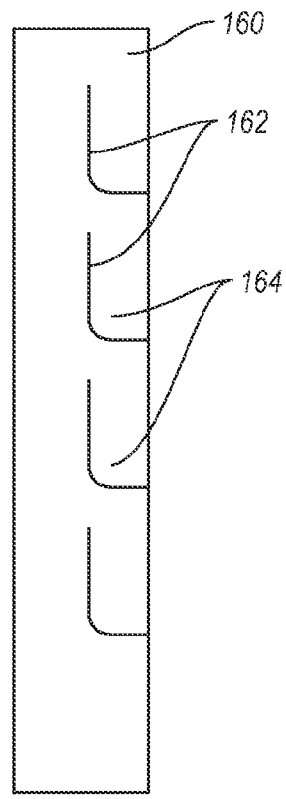
FIG. 4 illustrates an embodiment of an implantable lumen filter formed from a flat member.

FIGS. 3 and 4 illustrate various embodiments of implantable lumen filters manufactured from a tube and a flat member. These manufacturing techniques may be used with any of the filters described herein. For instance, the filter 100 shown in FIGS. 1 and 2 may be manufactured using these techniques.

The filter shown in FIG. 3 can be formed from a tube 150 that is cut into a spiral, helical, or other shape using the forming techniques described herein. The tube 150 shown in FIG. 3 is formed using laser cutting. The body of the filter can be formed in a continuous line 152 around the tube 150. Forming the body using laser cutting may include a single continuous cut, multiple intersecting cuts, other cuts, or combinations thereof. Additional forming may be performed to form sections 156 into impeding members (discussed in further detail below). For instance, material may be removed along a line 154 from the continuous line 152. The sections 156 may then be bent towards a central axis of the tube 150.

In another example, the filter can be manufactured from a strip 160 of material (as shown in FIG. 4) that may be rolled into a spiral, helical, or other shape. The strip 160 may be formed to include sections 164 that may be formed into impeding members. For instance, material may be removed from the strip 160 along a line 162. The sections 164 can be bent toward the desired position by forming and/or heat treating the material.

In another example, the filter body can be formed by rolling a wire to a flattened cross section (similar to the configuration shown in FIG. 4) and forming the impeding members from the flattened wire (as discussed below). The wire can also be round and rolled into a spiral, helical, or other shape. In other examples, the impeding members can be connected to the filter body by mechanical bonding, adhesives, thermal bonding, chemical bonding, combinations thereof, or other manufacturing techniques usable to mount, couple, or attach two medical components. The filter and its components can be formed from any of the materials described above.

FIGS. 5A and 5B illustrate an example of an implantable lumen filter 170. The filter 170 is shown in a partial cutaway flat state in FIG. 5A and a partial cutaway coiled state in FIG. 5B. The filter 170 may incorporate any of the features and/or components of any of the filters described herein.

The filter 170, in this example, may include a body 171 that coils (i.e. winds) in a spiral, helical, or other configuration. The body 171 may include impeding members 172, 173 having a first ends 172a, 173a and second ends 172b, 173b. The impeding members 172, 173 may be configured to extend from their first ends 172a, 173a towards the center (i.e. a central axis) of the filter 170. The impeding members 172, 173 may be bent towards the center of the filter 170 on one side of the body 171. The impeding members 172, 173 may be bent or otherwise oriented toward the center of the filter 170.

The impeding members 172, 173 are shown on the same side (i.e. the right side in FIG. 5A) of the body 171. In other embodiments, the impeding members 172, 173 may be positioned on the same side or differing sides and/or on the right or the left side of the body 171 as shown in FIG. 5A. A keyway 174 may be placed between the junction of the impeding member 173 and the body 171 to reduce stress near the joint.

Engaging portions 176, 177, 178 are shown connected to a different side (i.e. the left side as shown in FIG. 5A) of the body 171 than the impeding members 172, 173 (i.e. the right side as shown in FIG. 5A). In other embodiments, the impeding members 172, 173 and the engaging portions 176, 177, 178 may be positioned on the same side or differing sides and/or on the right or the left side of the body 171 as shown in FIG. 5A. The engaging portions 176, 177, 178 may extend from the body 171 away from the impeding members 172, 173. The impeding members 172, 173 and/or the engaging portions 176, 177, 178 may be bent into these orientations. The engaging portions 176, 177, 178 may be configured to engage and/or pierce tissue.

The engaging portions 176, 177, 178 may be arranged to engage an inner surface of a body lumen. The engaging portions 176, 177, 178, in the present embodiment, may be configured to pierce an inner surface of the body lumen. In other embodiments, the filter 170 may be configured to provide sufficient radial force to engage (without piercing) the inner surface of the body lumen. The filter 170 may be formed according to any of the manufacturing techniques described herein.

FIGS. 6A and 6B illustrate another example of an implantable lumen filter 180. These figures show the filter 180 in a partial cutaway flat state in FIG. 6A and a partial cutaway coiled state in FIG. 6B. The filter 180 may incorporate any of the features and/or components of any of the filters described herein.

The filter 180, in this example, may include a body 181 that coils (i.e. winds) in a spiral, helical, or other configuration. The body 181 may include impeding members 182, 183 having first ends 182a, 183a and second ends 182b, 183b. The impeding members 182, 183 may be configured to extend from their first ends 182a, 183a towards the center (i.e. a central axis) of the filter 180 on one side of the body 181. The impeding members 182, 183 may be bent or otherwise oriented toward the center of the filter 180.

The impeding members 182, 183 are shown on the different sides (i.e. the right and left side in FIG. 6A) of the body 181. In other embodiments, the impeding members 182, 183 may be positioned on the same side or differing sides and/or on the right or the left side of the body 181 as shown in FIG. 6A. Texturing 184, such as ridges or other surface texturing, may be placed on the impeding member 183 to assist in capturing, impeding, and/or lysing particulates in the bodily fluid stream.

Engaging portions 186, 187, 188 are shown connected to the same side (i.e. the right side as shown in FIG. 6A) of the body 181 as the impeding members 182, 183. In other embodiments, the impeding members 182, 183 and the engaging portions 186, 187, 188 may be positioned on the same side or differing sides and/or on the right or the left side of the body 181 as shown in FIG. 6A. The engaging portions 186, 187, 188 may be bent to extend out from the body 181 in a direction opposite to the impeding members 182, 183. The engaging portions 186, 187, 188 may be arranged to secure the filter 180 in a body lumen. The impeding members 182, 183 and/or the engaging portions 186, 187, 188 may be bent into these orientations.

FIGS. 7A and 7B illustrate a further example of an implantable lumen filter 190. These figures show the filter 190 in a partial cutaway flat state in FIG. 7A and a partial cutaway coiled state in FIG. 7B. The filter 190 may incorporate any of the features and/or components of any of the filters described herein.

The filter 190, in this example, includes a body 191 that coils (i.e. winds) in a spiral, helical, or other configuration. The body 191 may include at least one impeding member 192 having a first end 192a, a second end 192b, and an intermediate portion 192c. The first end 192a of the impeding member 192 may be connected to a portion of the body 191 and may extend to the second end 192b. The second end 192b may be connected to another portion of the body 191. The intermediate portion 192c of the impeding member 192 may be oriented toward the center (i.e. central axis) of the filter 190.

The impeding member 192 may be formed by cutting an aperture 194 into the body 191. The impeding member 192 may be bent near the junction where the aperture 194 meets the body 191 to extend a portion of the impeding member 192 towards the center of the filter 190 on one side of the body 191. The impeding members 192, in the present embodiment, may be integrally formed with the body 191. In other embodiments, the impeding members 192 may be attached to the body 191 near the first end 192a by welding, soldering, adhering, other attaching methods, or combinations thereof.

Engaging portions 196, 198 are shown connected to the same side (i.e. the right side as shown in FIG. 7A) of the body 191 as the impeding member 192. In other embodiments, the impeding member 192 and the engaging portions 196, 198 may be positioned on the same side or differing sides and/or on the right or the left side of the body 191 as shown in FIG. 7A. The engaging portions 196, 198 may be bent to extend out from the body 191 in a direction opposite to the impeding member 192. The engaging portions 196, 198 are arranged to secure the filter 190 in a body lumen.

FIGS. 8A and 8B illustrate a still further example of an implantable lumen filter 200. These figures show the filter 200 in a partial cutaway flat state in FIG. 8A and a partial cutaway coiled state in FIG. 8B. The filter 200 may incorporate any of the features and/or components of any of the filters described herein.

The filter 200, in this example, may include a body 201 that coils (i.e. winds) in a spiral, helical, or other configuration. The body 201 may include impeding members 204, 205 having first ends 204a, 205a, second ends 204b, 205b, and intermediate portions 204c, 205c. The first ends 204a, 205a of the impeding members 204, 205 may be connected to a portion of the body 201 and may extend to the second ends 204b, 205b. The second ends 204b, 205b may be connected to another portion of the body 201. The intermediate portions 204c, 205c of the impeding members 204, 205 may be oriented toward the center (i.e. central axis) of the filter 200.

The impeding members 204, 205 may be formed by cutting apertures 206, 207 into the body 201. The apertures 206, 207 may extend from the first ends 204a, 205a toward the second ends 204b, 205b of the impeding members 204, 205. The impeding members 204, 205 may be bent at the junction where the apertures 206, 207 meet the body 201 and along the impeding members 204, 205 to extend the impeding members 204, 205 towards the center of the filter 200 on one side of the body 201. Keyways 208, 209 may be placed between the junction of the impeding member 204 and the body 201 to reduce stress at the bend.

Figure 9:
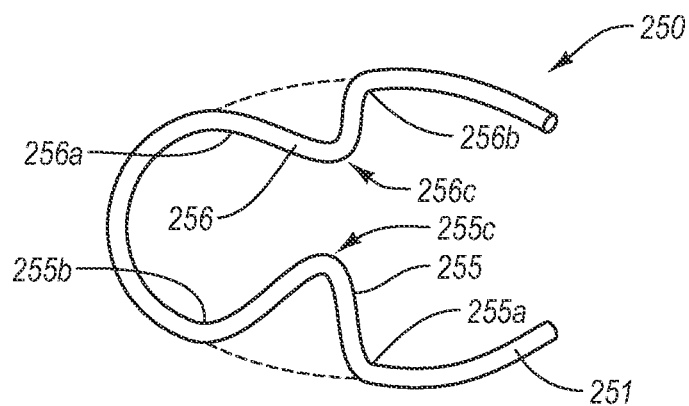
FIG. 9 is a partial cutaway view of yet another example of an implantable lumen filter.
Figure 10:
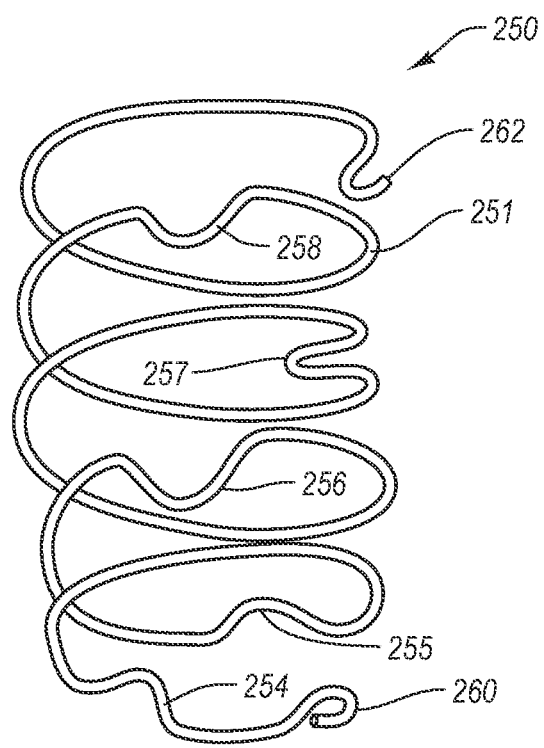
FIG. 10 is a side isometric view of the implantable lumen filter of FIG. 9.

FIGS. 9 and 10 illustrate yet another example of an implantable lumen filter 250. These figures show a filter 250 made of wire. The filter 250 may incorporate any of the features and/or components of any of the filters described herein.

The filter 250, in this example, includes a body 251 that coils (i.e. winds) in a spiral, helical, or other configuration. The body 251 may include impeding members 254, 255, 256, 257, 258 that may be formed by bending the body 251 towards the center (i.e. central axis) of the filter 250 at certain locations. As shown in FIG. 9, the impeding members 255, 256 may include first ends 255a, 256a, second ends 255b, 256b, and intermediate portions 255c, 256c. The impeding members 254, 255, 256, 257, 258 can be offset from each other to capture, inhibit, and/or lyse particulates at different sides of the filter 250. For instance, the impeding members 254, 255, 256, 257, 258 may be circumferentially offset about the center of the filter 250.

The filter 250 can include at least one retrieval portion 260, 262 near at least one end of the filter 250 to facilitate retrieval of the filter 250 from a body lumen by, for example, a retrieval mechanism (not shown). The retrieval portions 260, 262 may be formed by bending a loop around the ends of the wire structure of the body 251. Other retrieval mechanisms may be used.

Figure 11:
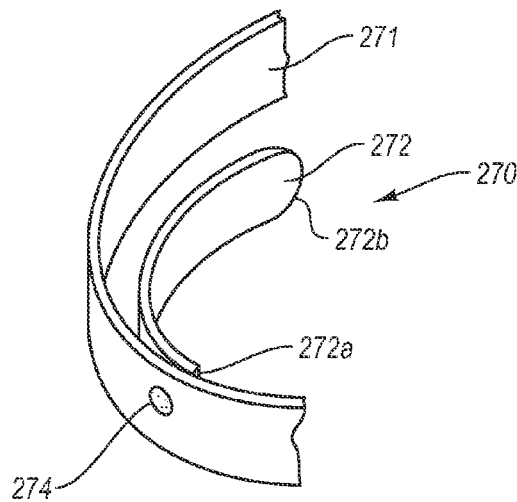
FIGS. 11-16 are partial cutaway views of various examples of implantable lumen filters.

FIG. 11 illustrates a partial cutaway view of a implantable lumen filter 270 with a connected impeding member 272. The filter 270 may incorporate any of the features and/or components of any of the filters described herein.

The impeding member 272 may include a first end 272a and a second end 272b. The impeding member 272 may be welded to a body 271 of the filter 270 near the first end 272a. The body 271 may be coiled (i.e. wound) in a spiral, helical, or other configuration without any impeding members 272 initially formed in the body 271. The impeding members 272 may be attached to the body 271 by welding, soldering, adhering, other attaching methods, or combinations thereof. For example, the impeding member 272 may be welded to the body 271 with a weld 274. The impeding members 272 may be arranged to extend towards the center (i.e. central axis) of the filter 270. In the present example, the narrowest portion of the impeding member 272 may be generally vertically aligned with the narrowest portion of the body 271. In other embodiments, the impeding member 272 and/or the body 271 may be otherwise oriented.

Figure 12:
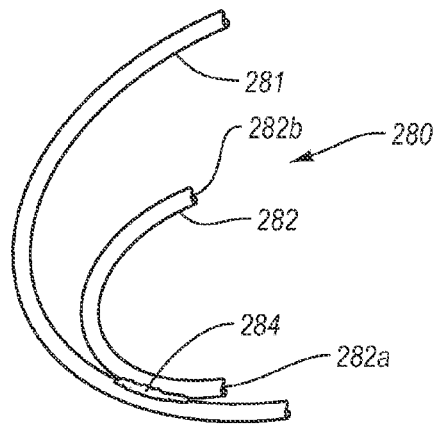

FIG. 12 illustrates a partial cutaway view of an implantable lumen filter 280 with a connected impeding member 282 made from wire. The filter 280 may incorporate any of the features and/or components of any of the filters described herein.

The impeding member 282 may include a first end 282a and a second end 282b. The body 281 may be coiled (i.e. wound) in a spiral, helical, or other configuration without any impeding member 282 initially formed in the body 281. The impeding member 282 may be attached to the body 281 near the first end 282a by welding, soldering, adhering, other attaching methods, or combinations thereof. For example, the impeding member 282 may be welded to the body 281 with a weld 284. The impeding member 282 may be oriented to extend towards the center (i.e. central axis) of the filter 280.

Figure 13:
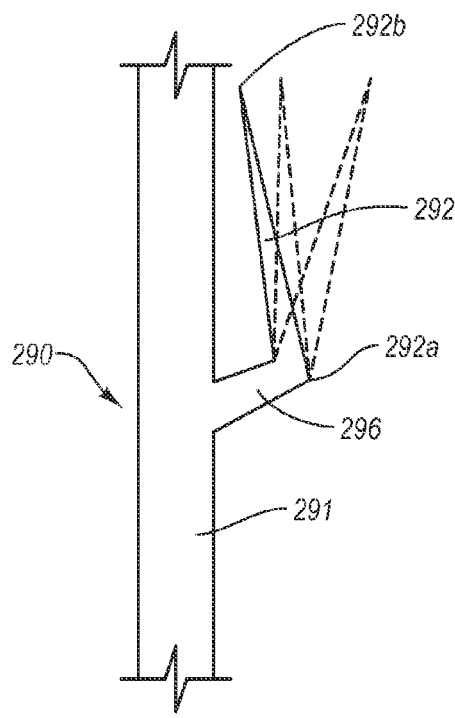

FIG. 13 illustrates an implantable lumen filter 290 with a tapered impeding member 292 shown in a partial cutaway flat state. The filter 290 may incorporate any of the features and/or components of any of the filters described herein.

The filter 290 may include a body 291 that may be coiled (i.e. wound) in a spiral, helical, or other configuration. The impeding member 292 may include a first end 292a and a second end 292b. The impeding member 292, in the present embodiment, may be integrally formed with the body 291. In other embodiments, the impeding members 292 may be attached to the body 291 near the first end 292a by welding, soldering, adhering, other attaching methods, or combinations thereof. The impeding member 292 may be bent towards the center (i.e. central axis) of the filter 290. The impeding member 292 may taper to a point near the second end 292b.

The impeding member 292 may include an extension 296 near the first end 292a. The extension 296 may provide a distance from the body 291 to angle the impeding member 292 towards the filter 290. The impeding member 292 can be configured to have an angle selected from a variety of angles to vary the distance and/or angle from the filter 290. The extension 296 can be arranged to extend the impeding member 292 out from the filter 290. The taper can be attached to the extension 296 and arranged to angle from the extension 296 towards the filter 290.

Figure 14:
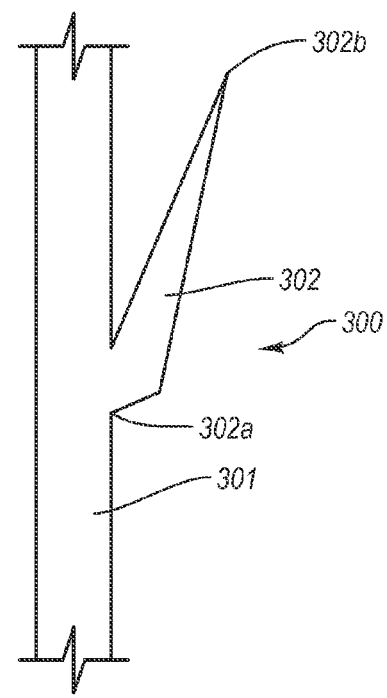

FIG. 14 illustrates an implantable lumen filter 300 with a tapered impeding member 302 shown in a partial cutaway flat state. The filter 300 may incorporate any of the features and/or components of any of the filters described herein.

The filter 300 may include a body 301 that may be coiled (i.e. wound) in a spiral, helical, or other configuration. The impeding member 302 may include a first end 302a and a second end 302b. The impeding member 302, in the present embodiment, may be integrally formed with the body 301. In other embodiments, the impeding member 302 may be attached to the body 301 near the first end 302a by welding, soldering, adhering, other attaching methods, or combinations thereof. The impeding member 302 may be bent towards the center (i.e. central axis) of the filter 300. The impeding member 302 may taper to a point near the second end 302b and may extend out from the filter 300.

Figure 15:
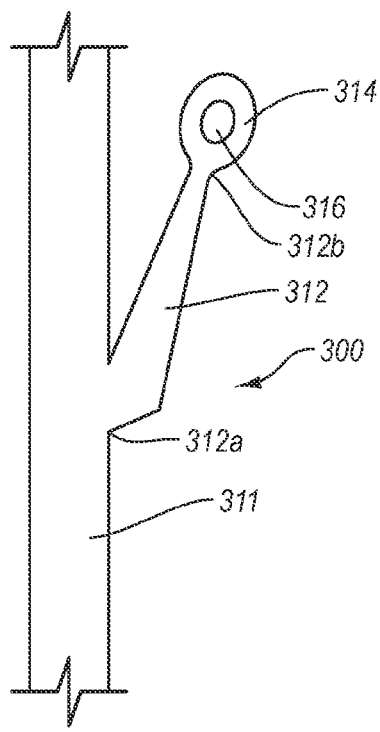

FIG. 15 illustrates an implantable lumen filter 310 with a tapered impeding member 312 shown in a partial cutaway flat state. The filter 310 may incorporate any of the features and/or components of any of the filters described herein.

The filter 310 may include a body 311 that may be coiled (i.e. wound) in a spiral, helical, or other configuration. The impeding member 312 may include a first end 312a and a second end 312b. The impeding member 312, in the present embodiment, may be integrally formed with the body 311. In other embodiments, the impeding member 312 may be attached to the body 311 near the first end 312a by welding, soldering, adhering, other attaching methods, or combinations thereof. The impeding member 312 may be bent towards the center (i.e. central axis) of the filter 310. The impeding member 312 may extend out from the body 311. The impeding member 312 may include an annular portion 314 near the second end 312b. The annular portion 314 can also include an aperture 316 to allow blood to flow through the aperture 316 and/or help capture, inhibit, and/or lyse particulates in the body lumen.

Figure 16:
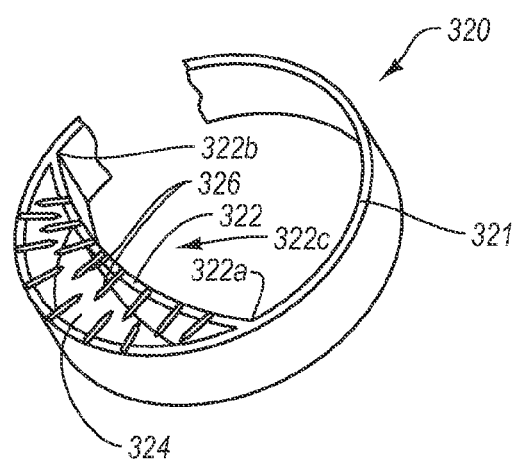

FIG. 16 illustrates a further example of an implantable lumen filter 320. The filter 320 may incorporate any of the features and/or components of any of the filters described herein.

The filter 320 may include a body 321 that may be coiled (i.e. wound) in a spiral, helical, or other configuration. The body 321 may include an impeding member 322 that may include a first end 322a, a second end 322b, and an intermediate portion 322c. The first end 322a of the impeding member 322 may be connected to a portion of the body 321 and may extend to the second end 322b. The second end 322b may be connected to another portion of the body 321. The intermediate portion 322c of the impeding member 322 may be oriented toward the center (i.e. central axis) of the filter 320.

The impeding member 322 may be formed by cutting an aperture 324 into the body 321 along the thickness of the body 321. The impeding member 322 may be bent at the junction where the aperture 324 meets the body 321 to extend the impeding member 322 in towards the center (i.e. central axis) of the filter 320. The impeding members 322, in the present embodiment, may be integrally formed with the body 321. In other embodiments, the impeding member 322 may be attached to the body 321 near the first end 322a by welding, soldering, adhering, other attaching methods, or combinations thereof.

Additional impeding members 326 may be integrally formed with and/or be connected to the body 321 and/or the impeding member 322 to extend within and/or without the aperture 324. Additional impeding members 326 may be attached to the body 321 and/or the impeding member 322 by welding, soldering, adhering, other attaching methods, or combinations thereof. The additional impeding members can be arranged to help capture, inhibit, and/or lyse particulates in a body lumen.

Figure 17:
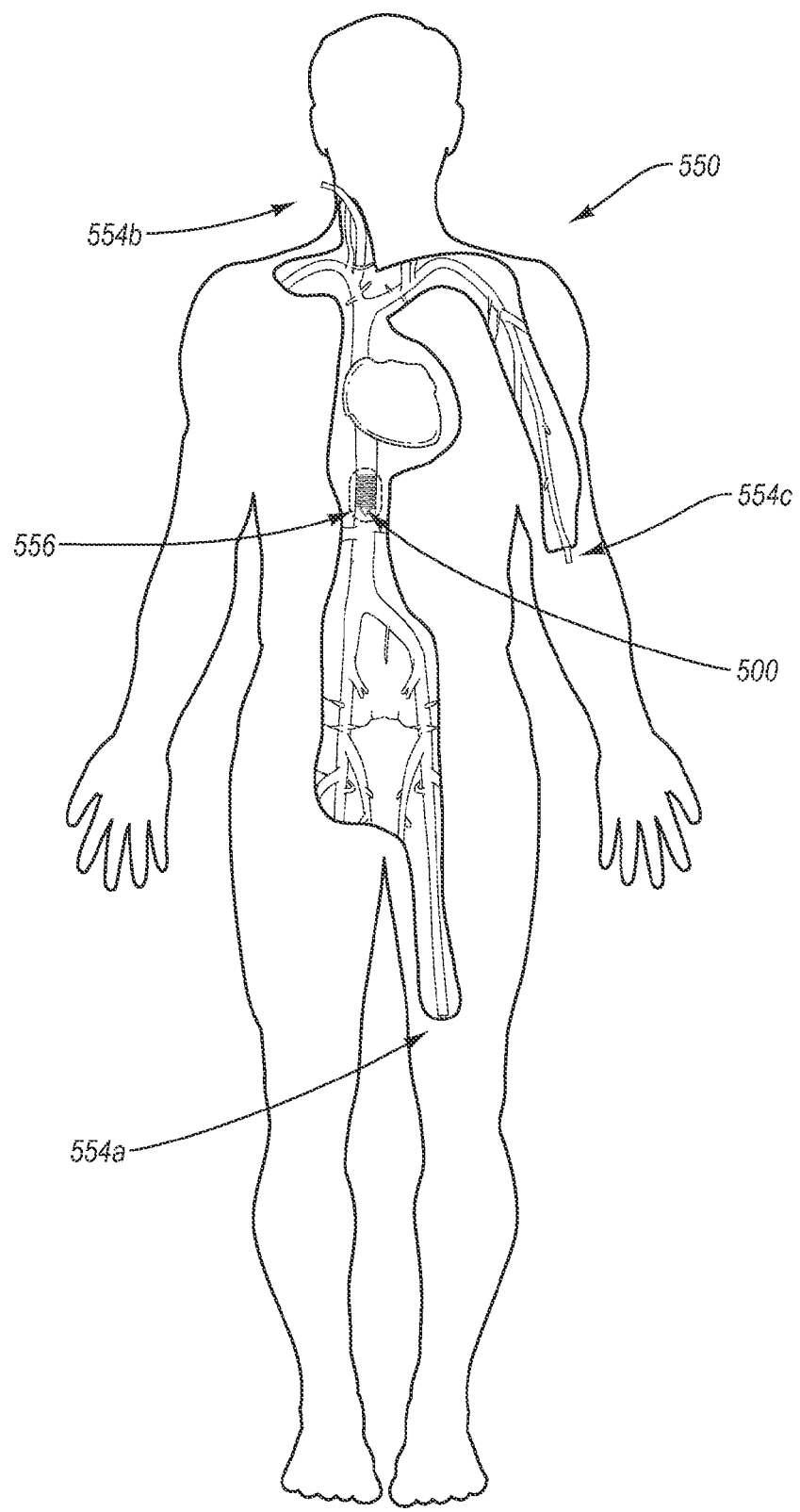
FIG. 17 illustrates an exemplary subject for an implantable lumen filter.

FIG. 17 illustrates an exemplary subject 550 for an implantable lumen filter 500. The implantable lumen filter 500 may be functionally similar to the implantable lumen filters 100, 170, 180, 190, 200, 250, 270, 280, 290, 300, 310, 320 previously described above and shown in FIGS. 1-2 and 5-16 and the implantable lumen filters 330, 350, 370, 390, 420, 440 described below and shown in FIGS. 18-22 and 24-25 in most respects, wherein certain features will not be described in relation to this configuration wherein those components may function in the manner as described above and are hereby incorporated into the configuration described below. The implantable lumen filter 500 may incorporate at least one component of the implantable lumen filters 100, 170, 180, 190, 200, 250, 270, 280, 290, 300, 310, 320, 330, 350, 370, 390, 420, 440 described in connection with FIGS. 1-2, 5A-16, 18-22, and 24-25, respectively.

Although many of the embodiments herein may describe an implantable lumen filter 500, other filters may be deployed and/or retrieved using at least one embodiment of a filter retrieval system described herein. The filter 500 may be implanted in a body lumen of the subject 550. The filter 500 may be inserted and/or retrieved through an access site 554a, 554b, 554c. In the present embodiment, the access site may include a femoral artery access site 554a, a jugular vein access site 554b, a radial vein access site 554c, femoral vein, brachial vein, brachial artery, other access sites, or combinations thereof. For instance, the filter 500 may be inserted through the femoral artery access site 554a and retrieved through the jugular or radial vein access site 554b, 554c. In another example, the filter 500 may be inserted through the jugular vein access site 554b and retrieved through the femoral artery or radial vein access site 554a, 554c. In a further example, the filter 500 may be inserted through the radial vein access site 554c and retrieved through the femoral artery or jugular vein access site 554a, 554b.

The filter 500 may be inserted and retrieved through the radial vein access site 554c. Additionally, the filter 500 may be inserted and retrieved through the jugular vein access site 554b. Further, the filter 500 may be inserted and retrieved through the femoral artery access site 554a.

The filter 500 may be deployed near a deployment site 556. In the present embodiment, the deployment site 556 may include a location within the inferior vena cava. In other embodiments, other deployment sites may be used, such as the superior vena cava. For example, the deployment site 556 may include all larger veins.

Some implantable lumen filters typically use jugular, antecubital, or other access sites for retrieval because they are typically not configured to be retrieved through the femoral access. Retrieval through the same access site through which the filter was deployed may be desired. At least one embodiment of a filter retrieval system may provide for retrieval through the same access site through which the filter was deployed.

Figure 18:
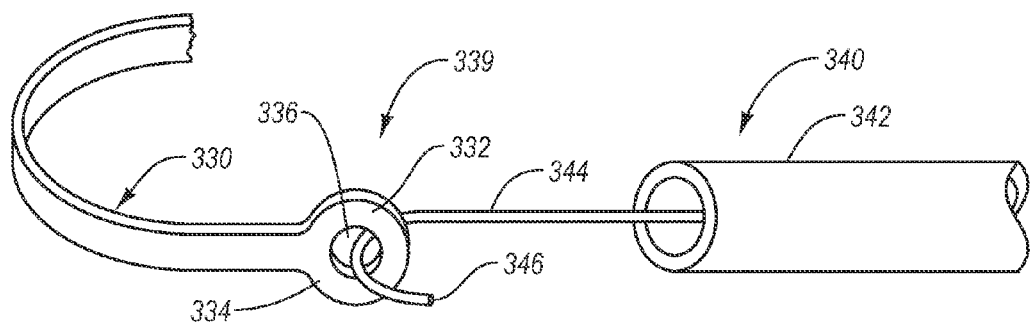
FIGS. 18-19 illustrate exemplary embodiments of retrieving mechanisms for implantable lumen filters.
Figure 19:
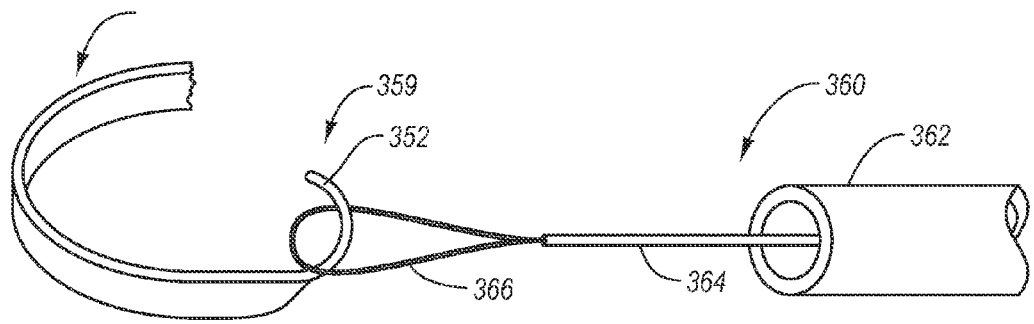

FIGS. 18 and 19 illustrate a mechanism for retrieving a filter from a body lumen. As shown in the partial cutaway view of FIG. 18, a filter 330 may include a retrieval portion 339. The filter 330 may incorporate any of the features and/or components of any of the filters described herein. The retrieval portion 339 may include an eyelet 332. The eyelet 332 may include a round end 334 with an aperture 336 through it. The eyelet 332 may be positioned near at least one end of the filter 330.

A retrieving mechanism 340 may include a tube 342 configured to receive the filter 330. The retrieving mechanism 340 may be guided through the body lumen to a deployment site where the filter 330 may be located. The retrieving mechanism 340 may include a wire 344 that may include a retrieval member 346 configured to engage the retrieval portion 339. The retrieval member 346 may be hooked or otherwise shaped and is shown in hook shape in FIG. 18. The wire 344 may be directed to the filter 330 to engage the retrieval member 346 with the retrieval portion 339. The retrieval member 346, in the present embodiment, may engage the aperture 334 of the eyelet 332. The filter 330 may be directed toward the tube 342 to receive at least a portion of the filter 330 and/or remove the filter 330 from the body lumen.

In the partial cutaway view of FIG. 19, a filter 350 may include a retrieval portion 359. The filter 350 may incorporate any of the features and/or components of any of the filters described herein. The retrieval portion 359 may include a retrieval element 352 that may be hooked or otherwise shaped and is shown in hook shape in FIG. 19. The retrieval element 352 may be positioned near at least one end of the filter 350.

A retrieving mechanism 360 may include a tube 362 configured to receive the filter 350. The retrieving mechanism 360 may be guided through the body lumen to a deployment site where the filter 350 may be located. The retrieving mechanism 360 may include a wire 364 that may include a retrieval member 366 configured to engage the retrieval portion 359. The wire 364 may include a retrieval member 366 configured to engage the retrieval portion 359. The retrieval member 366 may be shaped like a snare or may be otherwise shaped. The wire 364 can be directed to the spiral filter 350 to engage the retrieval element 352 with the retrieval member 366. The filter 350 may be directed toward the tube 362 to receive at least a portion of the filter 350 and/or remove the filter 350 from the body lumen. The retrieval member 366 may be used to engage a filter 350 by encircling the retrieval member 366 around a loop or other portion of the filter 350.

Figure 20:
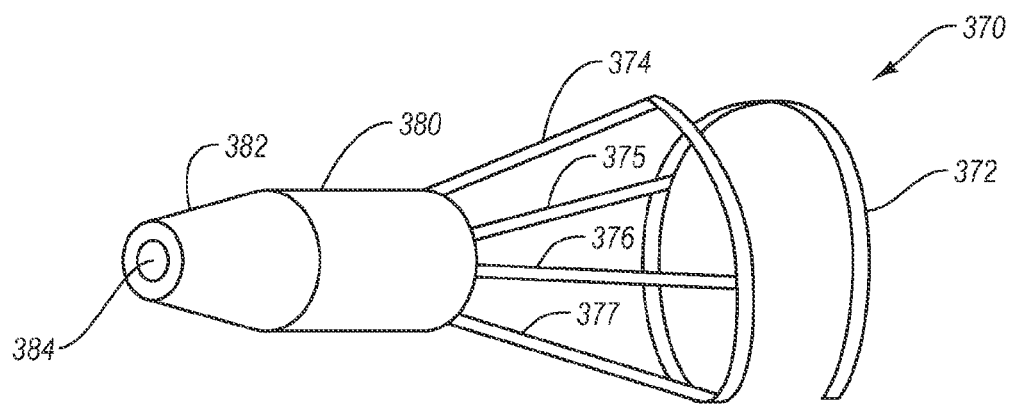
FIGS. 20-21 are partial cutaway views of various examples of implantable lumen filters.

FIG. 20 is a partial cutaway view of an end of an embodiment of an implantable lumen filter 370. The filter 370 may incorporate any of the features and/or components of any of the filters described herein.

The filter 370 may include a body 372 that coils (i.e. winds) in a spiral, helical, or other configuration. Impeding members 374, 375, 376, 377 may be positioned around a loop of the body 372. The impeding members 374, 375, 376, 377, in the present embodiment, may be positioned near one end of the filter 370. The members 374, 375, 376, 377 may be spaced around the body 372 at various orientations and are shown with a spacing of about 90 degrees and radiating toward the center (i.e. central axis) of the filter 370 in a generally circular fashion. The members 374, 375, 376, 377 may extend outward (i.e. away from the central axis) from the end of the filter 370 and may be configured to impinge upon the bodily fluid flow through the body lumen.

A bushing 380 may be attached to at least one end of the members 374, 375, 376, 377 on a side opposite the body 372. The bushing 380 may include a head 382 that may be conical, may taper to a smaller diameter, or may taper to a point at one end (i.e. a spherical, oblong, pointed, or otherwise shaped head). The bushing 380 may include a hollow core 384 that may extend from one end toward the other end and is shown extending through the length of the bushing 380. The bushing 380 may be used to facilitate retrieval of the filter 370 by receiving at least a portion of a retrieving mechanism (such as the retrieving mechanism 400 described in conjunction with FIG. 22) into the hollow core 384.

Figure 21:
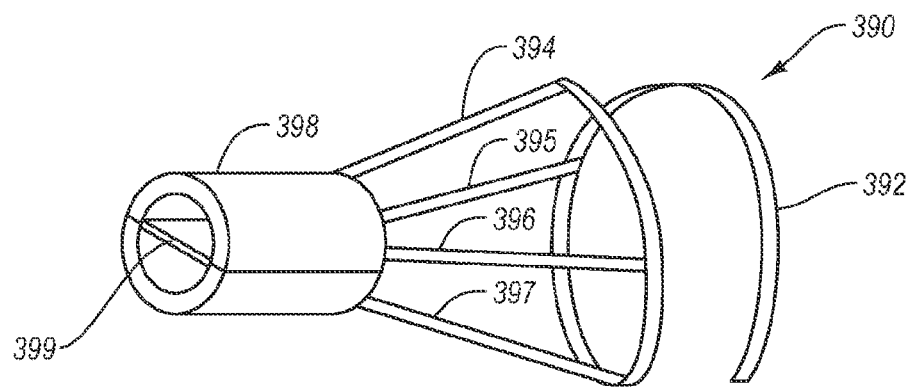

FIG. 21 is a partial cutaway view of an end of another embodiment of a filter 390. The filter 390 may incorporate any of the features and/or components of any of the filters described herein.

The filter 390 may include a body 392 that coils (i.e. winds) in a spiral, helical, or other configuration. Impeding members 394, 395, 396, 397 may be positioned around a loop of the body 392 near one end of the filter 390. The members 394, 395, 396, 397 may be spaced around the body 392 at various orientations and are shown with a spacing of about 90 degrees and radiating toward the center (i.e. central axis) of the filter 390 in a generally circular fashion. The members 394, 395, 396, 397 may extend outward (i.e. away from the central axis)

from the end of the filter 390 and may be configured to impinge upon the bodily fluid flow through the body lumen.

A bushing 398 may be attached to at least one end of the members 394, 395, 396, 397 on a side opposite the body 392. The bushing 398 can have a tube configuration with a plate 399 from one end of the bushing 398 to the other. The bushing 398 may be used to facilitate retrieval of the filter 390 by receiving at least a portion of a retrieving mechanism (such as the retrieving mechanism 400 described in conjunction with FIG. 22) into lumen of the bushing 398. The plate 399 may limit the motion of a retrieving mechanism in at least one direction.

Figure 22:
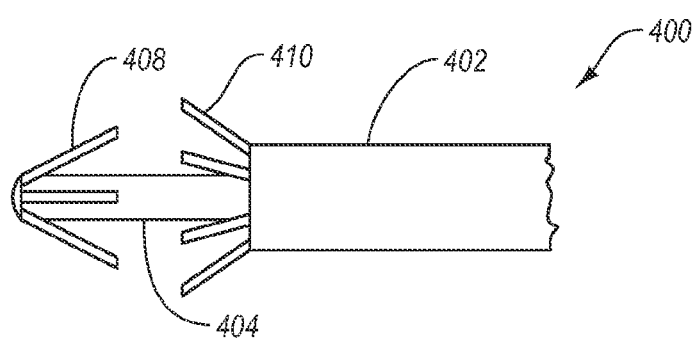
FIG. 22 illustrates another example of retrieving mechanism for implantable lumen filters.

FIG. 22 is a detailed view of an embodiment of a retrieving mechanism 400. The retrieving mechanism 400 may include a tube 402 and a member 404 extending through the tube 402. Rear facing pushing members 408 may be positioned at or near the end of the member 404 and may be oriented to generally extend toward the tube 402. The rear facing pushing members 408 may be flexible to move toward the member 404 while sliding into a hollow core, lumen, or other portion of a bushing (such as bushing 380 of the filter 370 shown in FIG. 20) or other component of a filter. After the rear facing pushing members 408 extend through the bushing, the rear facing pushing members 408 may expand. For instance, the rear facing pushing members 408 may extend past the outer diameter of the bushing. The rear facing pushing members 408 may be used to disengage and/or remove a filter from a body lumen.

Forward facing pushing members 410 can be attached to the member 404 at or near the tube 402. The forward facing pushing members 410 may be used to direct a filter forward to adjust the filter within a body lumen or to remove the filter from the body lumen. The forward facing pushing members 410 may be used to capture a filter in conjunction with the rear facing pushing members 408 to limit a portion of the filter from moving along the member 404.

Figure 23:
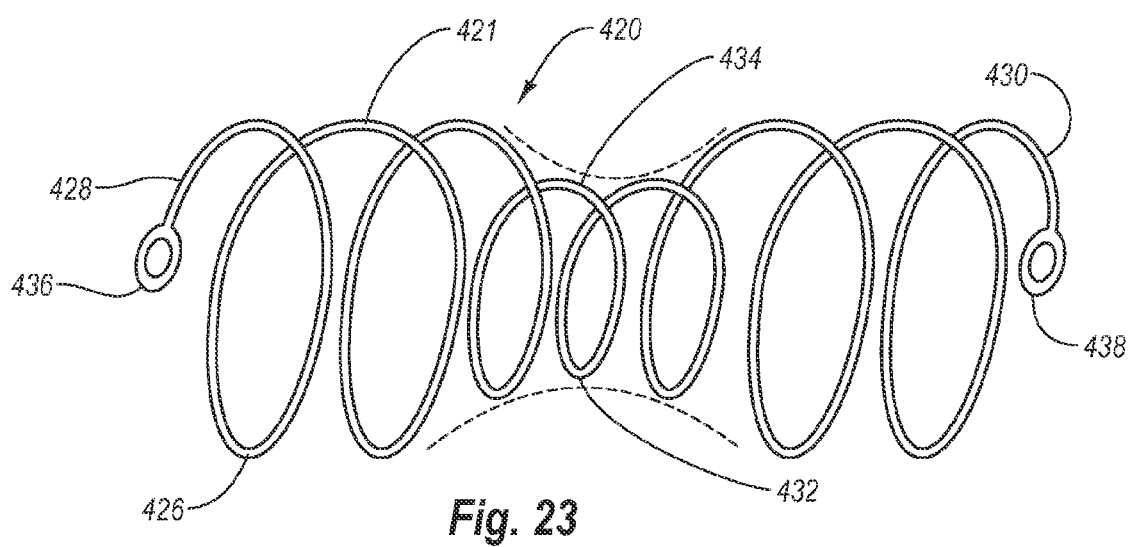
FIGS. 23-24 are side views of various examples of implantable lumen filters.

FIG. 23 illustrates a further embodiment of an implantable lumen filter 420. The filter 420 may include a body 421 that coils (i.e. winds) in a spiral, helical, or other configuration. As shown in FIG. 23, the body 421 coils in a spiral configuration. The filter 420 may incorporate any of the features and/or components of any of the filters described herein.

The body 421 and/or loops may have various shapes and/or sizes and is shown in an hourglass shape with varying loop sizes. As shown in FIG. 23, loops 426 on ends 428, 430 of the filter 420 may have a larger diameter than loops 432 in an immediate portion 434 generally forming an hourglass configuration as indicated by the dotted lines. The hourglass configuration may facilitate the self-aligning of the filter 420 within the body lumen. The loops of the body 421 of the filter 420 may vary between the ends 428, 430 and/or the intermediate portion 434.

The filter 420 may include retrieval portions 436, 438 that may be positioned near the ends 428, 430 of the body 421. The retrieval portions 436, 438, as discussed above, may facilitate retrieval of the filter 420 from the body lumen.

Figure 24:
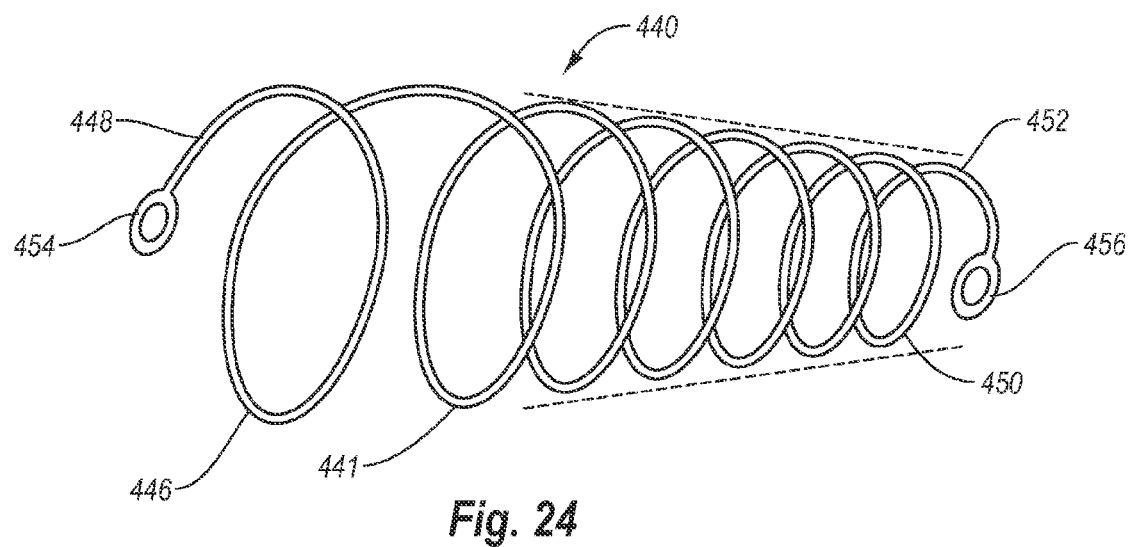

FIG. 24 illustrates a still further embodiment of an implantable lumen filter 440. The filter 440 may include a body 441 that coils (i.e. winds) in a spiral, helical, or other configuration. As shown in FIG. 24, the body 441 coils in a spiral configuration with varying loop sizes. The filter 440 may incorporate any of the features and/or components of any of the filters described herein.

The body 441 and/or loops may have various shapes and/or sizes and is shown in a generally conic shape with varying loop sizes. Loops 446 on one end 448 of the filter 440 may have a larger diameter than loops 450 on the opposing end 452. The conic configuration may facilitate aligning of the filter 440 since the larger loops may contact the body lumen while the smaller loops may remain suspended within the body lumen.

The filter 440 may include retrieval portions 454, 456 that may be positioned near the ends 448, 452 of the body 441. The retrieval portions 454, 456, as discussed above, may facilitate retrieval of the filter 440 from the body lumen.

FIGS. 25A-25G illustrate various steps in the deployment of an implantable lumen filter 800. The implantable lumen filter 800 may be functionally similar to the implantable lumen filters 100, 170, 180, 190, 200, 250, 270, 280, 290, 300, 310, 320 previously described above and shown in FIGS. 1-2, 5-16, 18-21, and 23-24 in most respects, wherein certain features will not be described in relation to this configuration wherein those components may function in the manner as described above and are hereby incorporated into the configuration described below. The implantable lumen filter 800 may incorporate at least one component of the implantable lumen filters 100, 170, 180, 190, 200, 250, 270, 280, 290, 300, 310, 320 described in connection with FIGS. 1-2, 5-16, 18-21, and 23-24, respectively.

Figure 25A:
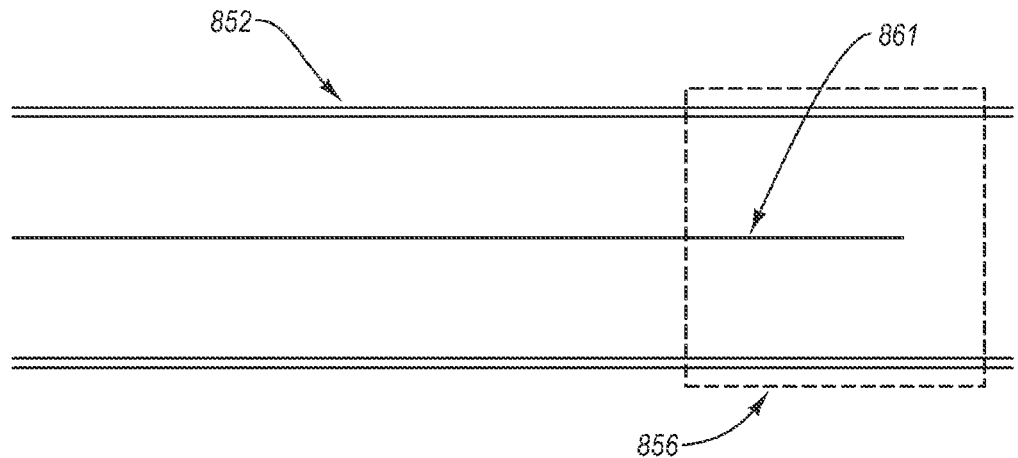
FIGS. 25A-25G' illustrate various steps in the deployment and retrieval of an example implantable lumen filter.

FIG. 25A illustrates a deployment site 856 within a body lumen 852 with a guidewire 861 partially inserted therethrough. The guidewire 861 may be inserted through an access site (shown as 554a, 554b, 554c in FIG. 17) toward the deployment site 856. The guidewire 861 may be used to locate the deployment site 856. In other configurations, other methods may be used in addition to or instead of a guidewire 861. For example, an imaging device, such as a fluoroscope, x-ray, and/or other imaging device may be used to locate the deployment site 856.

Figure 25B:
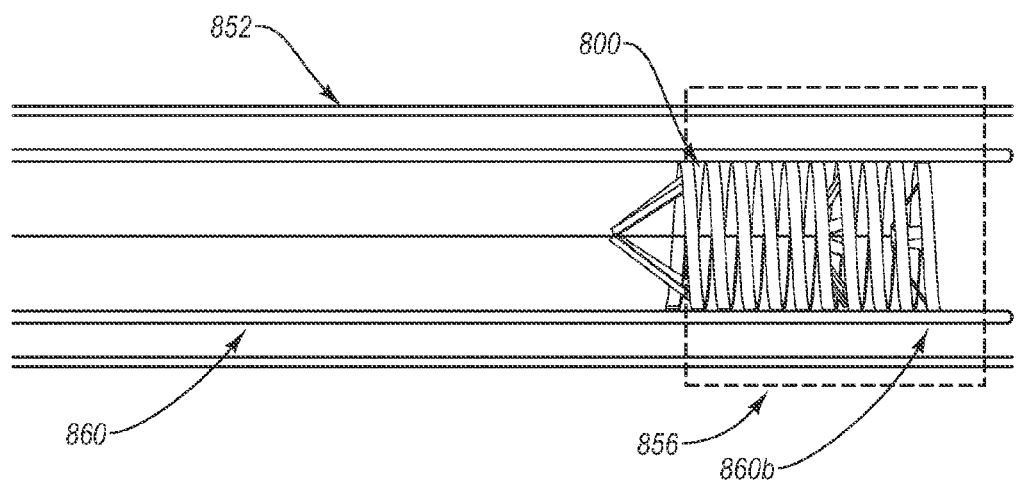

As shown in FIG. 25B, a delivery apparatus 860 may use the guidewire 861 to guide a distal end 860b of the delivery apparatus 860 toward the deployment site 856. An implantable lumen filter 800 may be disposed within the delivery apparatus 860. The implantable lumen filter 800, in the illustrated configuration, may be disposed within the delivery apparatus 860 while in a compressed state. While in the compressed state, the implantable lumen filter 800 may be longitudinally elongated with respect to a deployed state.

The guidewire 861 may be removed after the distal end 860b of the delivery apparatus 860 is located near the deployment site 856. Alternatively, the guidewire 861 may remain.

Figure 25C:
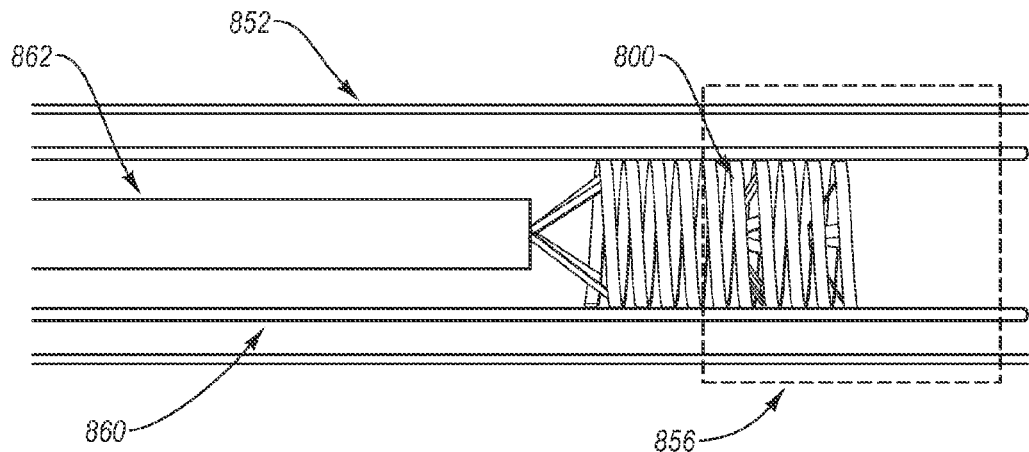

A deployment member 862 may be inserted through the delivery apparatus 860, as shown in FIG. 25C. The deployment member 862 may be used to deploy the implantable lumen filter 800. The implantable lumen filter 800 shown in FIG. 25C is similar to the implantable lumen filter 100 shown in FIGS. 1-2. In the configuration shown in FIG. 25D, the deployment member 862 may urge the implantable lumen filter 800 toward the distal end 860b of the delivery apparatus 860 while the delivery apparatus 860 may remain generally stationary.

The deployment member 862 may urge the implantable lumen filter 800 by abutting the proximal end 802a of the filter 800. The deployment member 862 may include a receiving area (not shown), such as a convex portion configured and dimensioned to receive the proximal end 802a, to facilitate urging the implantable lumen filter 800 out of the delivery apparatus 860. As the implantable lumen filter 800 begins to exit the delivery apparatus 860, the filter 800 may begin to transition from the compressed state shown in FIG. 25C toward a deployed state.

A deployment member 862' may be inserted through the delivery apparatus 860', as shown in FIG. 25C. The deployment member 862' may be used to deploy the implantable lumen filter 800'. The implantable lumen filter 800' shown in FIG. 25C' is similar to the implantable lumen filter 420 shown in FIG. 23. In the configuration shown in FIG. 25D', the deployment member 862' may urge the implantable lumen filter 800' toward the distal end 860b' of the delivery apparatus 860' while the delivery apparatus 860' may remain generally stationary.

The deployment member 862' may urge the implantable lumen filter 800' by abutting the proximal end 802a' of the filter 800'. The deployment member 862' may include a receiving area (not shown), such as a convex portion configured and dimensioned to receive the proximal end 802a', to facilitate urging the implantable lumen filter 800 out of the delivery apparatus 860'. As the implantable lumen filter 800' begins to exit the delivery apparatus 860', the filter 800' may begin to transition from the compressed state shown in FIG. 25C' toward a deployed state.

Figure 25D:
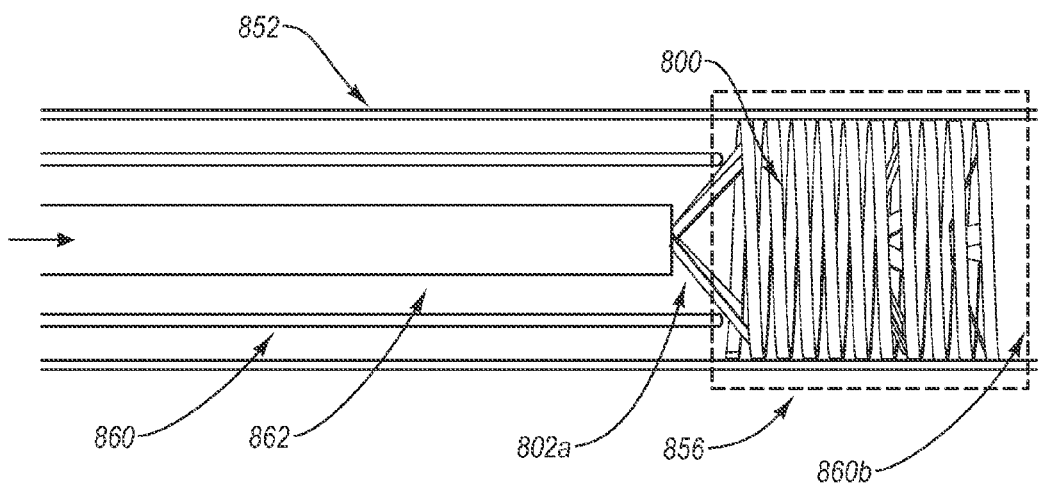
Figure 25C:
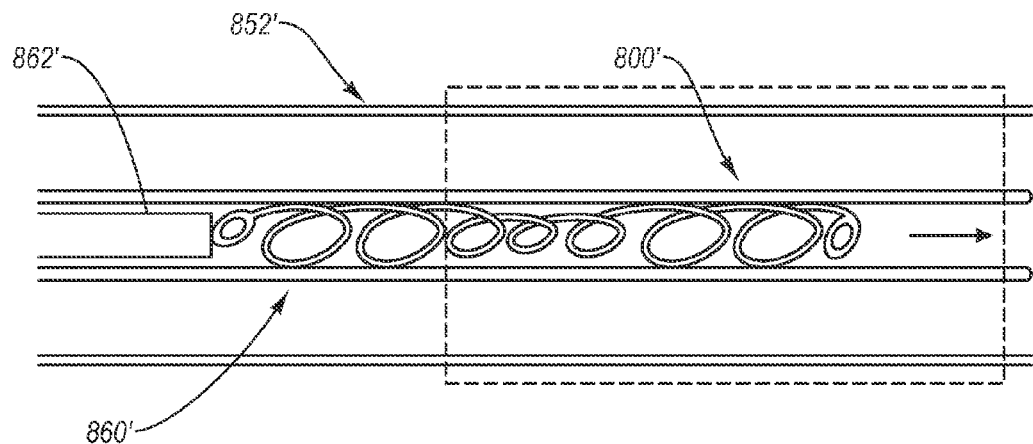
Figure 25D:
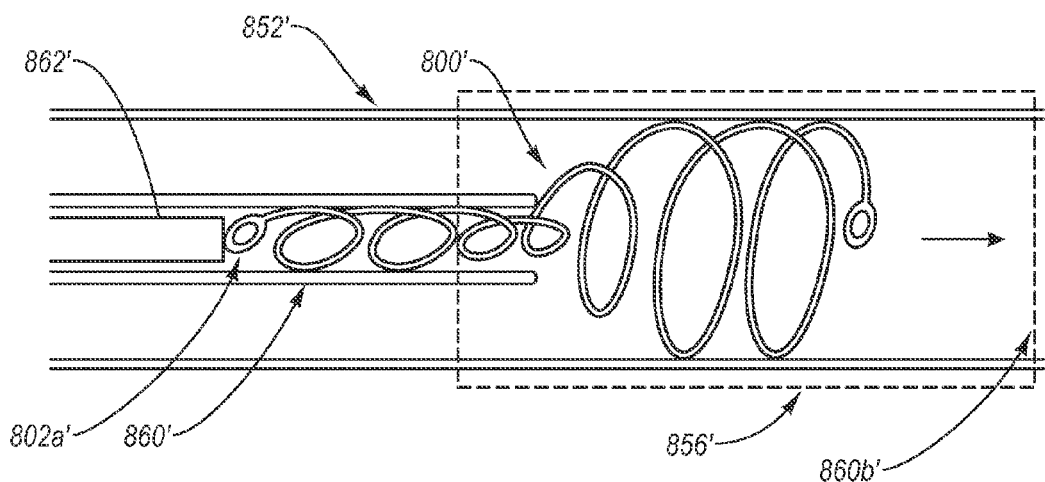

In the configuration shown in FIG. 25D", the delivery apparatus 860' may be retracted while the deployment member 862' may remain generally stationary. In other configurations, the delivery apparatus 860' and/or the deployment member 862' may cooperate to facilitate deployment of the implantable lumen filter 800'. For instance, the delivery apparatus 860' may be retracted while the deployment member 862' may urge the implantable lumen filter 800' toward the distal end 860b' of the delivery apparatus 860'. As the implantable lumen filter 800' begins to exit the delivery apparatus 860', the filter 800' may begin to transition from the compressed state shown in FIG. 25C' toward a deployed state.

Figure 25E:
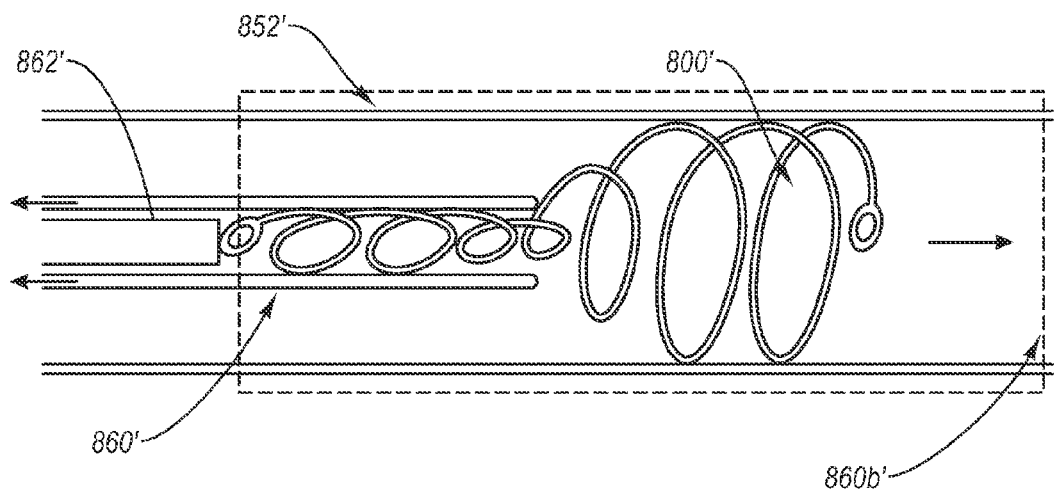
Figure 25E:
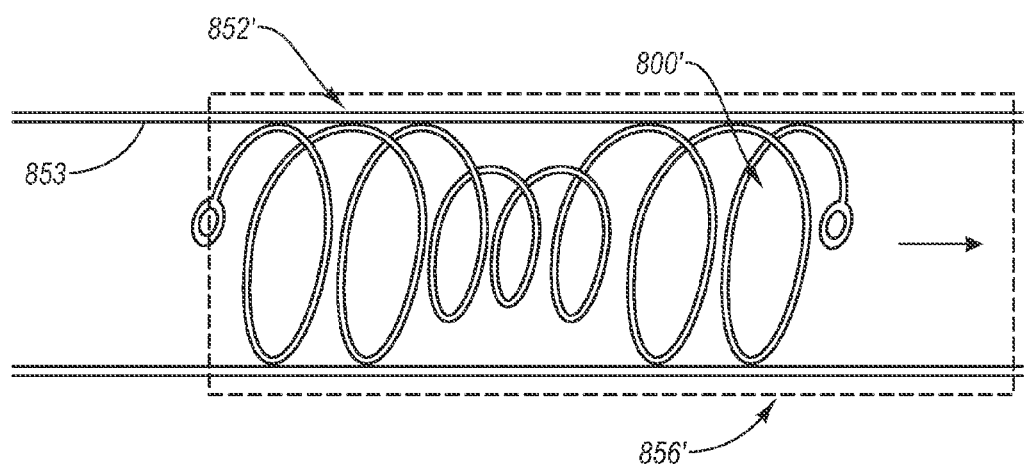

FIG. 25E illustrates a deployed implantable lumen filter 800 within the body lumen 852. In the deployed configuration, the implantable filter 800 may engage an inside surface 853 of the body lumen 852. In the deployed configuration, the implantable lumen filter 800 may be longitudinally reduced with respect to a collapsed configuration.

Figure 25F:
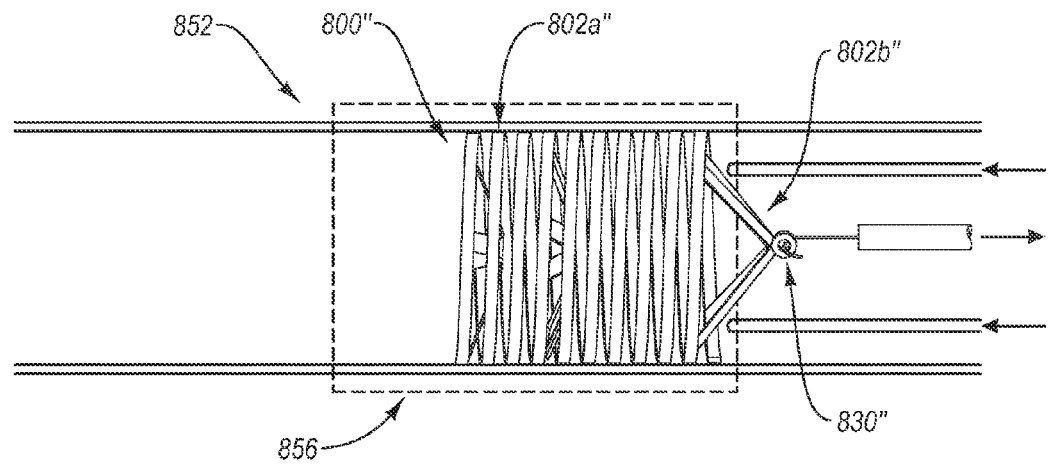
Figure 25F:
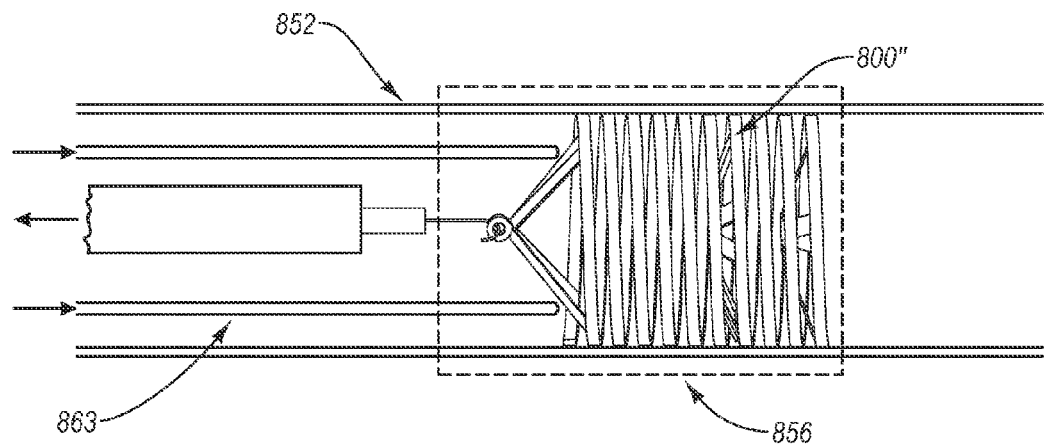
Figure 25G:
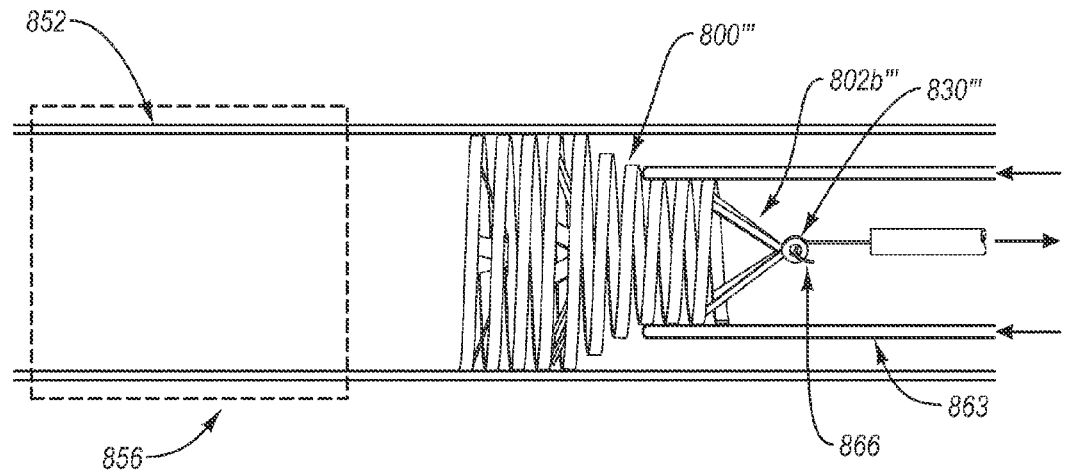
Figure 25G:
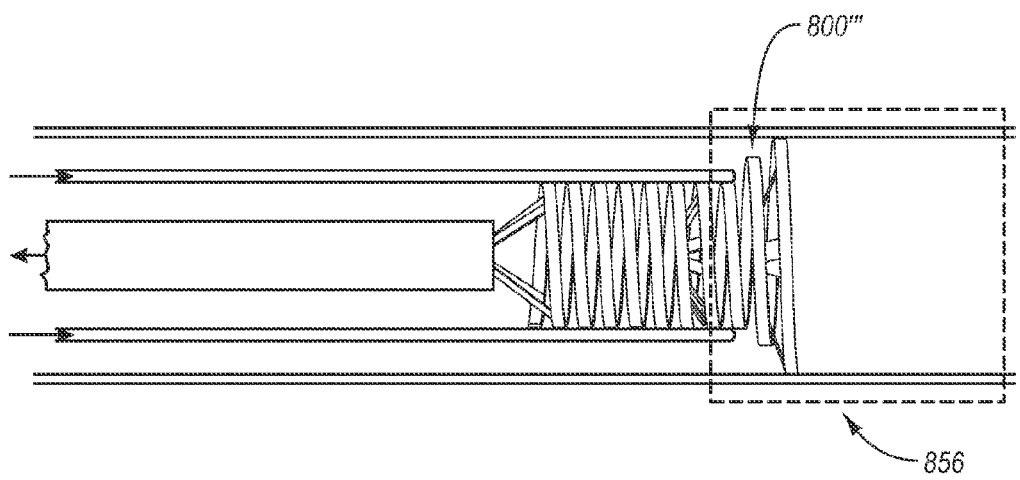

The implantable lumen filter 800" shown in FIGS. 25F-25G may include a retrieval portion 830" near the distal end 802b" of the implantable lumen filter 800". The retrieval portion 830" may be operatively connected to the distal end 802b" of the implantable lumen filter 800".

The implantable lumen filter 800" may be engaged by a retrieval member 864. The retrieval member 864 may include a retrieving mechanism 866, such as a hook, snare, other retaining mechanism, or combinations thereof, configured to engage the retrieval portion 830". For instance, the retrieval member 864 may be similar to the retrieval members 346, 366 described in connection with FIGS. 18-19. In other embodiments, the retrieval member 860 may be similar to the retrieval member 400 described in connection with FIG. 22.

Upon engaging the retrieval portion 830", the retrieval member 864 may urge the implantable lumen filter 800" into the retrieval apparatus 863. For example, urging the implantable lumen filter 800" toward the retrieval apparatus 863 may transition the filter 800" toward the compressed state.

In the illustrated configuration, the retrieval apparatus 863 and the retrieval member 864 may both move in generally opposite directions to urge the implantable lumen filter 800" into the retrieval apparatus 863 into a compressed state, such that the implantable lumen filter 800" may be longitudinally elongated with respect to a deployed state, as shown in FIG. 25G.

The implantable lumen filter 800''' shown in FIGS. 25F'-25G' is shown with a retrieval portion 830' near the proximal end 802a''' of the implantable lumen filter 800'''. The retrieval portion 830''' may be similar to the retrieval member 400 described in connection with FIG. 22. In other embodiments, the retrieval portion 830' may be similar to the retrieval portions 339, 359 described in connection with FIGS. 18-19.

The implantable lumen filters 800' may be engaged by a retrieval member 864. The retrieval member 864 may include a retrieving mechanism 866, such as a hook and/or other retaining mechanism, configured to engage the retrieval portion 830'''.

Upon engaging the retrieval portion 830', the retrieval member 864 may limit motion away from the retrieval member 864. In the illustrated configuration, the retrieval member 864 may remain generally stationary while the retrieval apparatus 863 is advanced to urge the implantable lumen filter 800' into the retrieval apparatus 863.

In the present configuration, the retrieval member 864 remains generally stationary while the retrieval apparatus 863 moves to urge the implantable lumen filter 800''' into the retrieval apparatus 863 into a compressed state, such that the implantable lumen filter 800' may be longitudinally elongated with respect to a deployed state, as shown in FIG. 25G'. In other configurations, both the retrieval apparatus 863 and the retrieval member 864 may move in generally opposite directions.

After the implantable lumen filters 800, 800', 800", 800' are within the retrieval apparatus 863, the retrieval apparatus 863 and implantable lumen filters 800, 800', 800", 800''' may be withdrawn through an access site (shown as 554a, 554b, 554c in FIG. 17).

In other embodiments, a filter may be expanded with a balloon to fit against a body lumen. Once in place, the catheter delivery system can be retracted and the radial members can spring into position after the balloon is deflated. The body and the radial members can have a different spring property by annealing the material in certain locations differently to encode the springing properties into the components of the filter by applying different transformation temperatures to the material.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. An implantable lumen filter comprising:
a body formed from an elongate member having a cylindrical, spiral configuration having loops encircling an axis extending along a length of said body, said body being sized to be implanted into a body lumen, said body being configured to transition from a compressed cylindrical state to a deployed cylindrical state; and
a first group of a plurality of members positioned around at least one loop of said body at a first position along the axis, said first group of the plurality of members being oriented towards the axis at a first angle, said first group of the plurality of members being arranged to lyse particulates of a selected size;
a second group of a plurality of members positioned around at least one loop of said body at a second position along the axis, and radiating towards the axis of said filter at a second angle, said second group of the plurality of members being oriented to capture or inhibit the particulates of another selected size from passing through said body, said second group of the plurality of members being dimensioned to allow blood components smaller than the selected size and the another selected size to pass through said body;

where the second group of the plurality of members is offset a distance from the first group of the plurality of members along the length of the body; and where the first angle at which the first group of the plurality of members is oriented toward the axis is different than the second angle at which the second group of the plurality of members radiates toward the axis.

2. The implantable lumen filter of claim 1, further comprising an engaging portion configured to engage an inner surface of a body lumen, said engaging portion including at least one of at least one tissue piercing portion configured to pierce at least a portion of an inner surface of the body lumen and at least one tissue engaging portion configured to engage but not pierce at least a portion of the inner surface of the body lumen.

3. The implantable lumen filter of claim 2, wherein said engaging portions are connected to a side of said body to which said first group and/or said second group of a plurality of members is connected, said engaging portions being bent to extend out from said body in a direction opposite to said first group and/or second group of a plurality of members.

4. The implantable lumen filter of claim 1, wherein said body includes ends and an intermediate portion, said loops of said body being larger at an end than at said intermediate portion and/or said loops of said body being larger at both ends than at said intermediate portion.

5. The implantable lumen filter of claim 1, wherein said body includes opposing ends, said loops of the body being larger at one end than the opposing end.

6. The implantable lumen filter of claim 1, further comprising a retrieval portion configured to facilitate retrieval of said implantable lumen filter from the body lumen.

7. The implantable lumen filter of claim 1, wherein said second group of said plurality of members is oriented toward the axis of said filter at a steep incline to direct particulates away from the axis and towards said body.

8. The implantable lumen filter of claim 1, wherein said second group includes more members than said first group of members.

9. The implantable lumen filter of claim 1, further comprising a filter material attached to and spanning across said members.

10. The implantable lumen filter of claim 1, further comprising a keyway placed between a junction between said member and said body.

11. The implantable lumen filter of claim 1, further comprising ridges formed on said members of said first group and/or said second group and configured to assist in capturing, inhibiting, and/or lysing particulates.

12. The implantable lumen filter of claim 1, wherein said members of said first group and/or said second group each have a first end that is attached to the body and a second end configured to extend towards the axis that tapers to a point, with the point configured to assist the members in capturing or lysing particulates in the blood stream.

13. The implantable lumen filter of claim 1, further comprising a round end at an end of one of said members of said first group and/or said second group, an aperture formed through a round end at an end of said one of said members of said first group and/or said second group, a retrieval portion, a hook, a bushing, a bushing with a conical head and a hollow core extending through a length of said bushing, a bushing having a tube configuration with a plate extending through said bushing, or a combination thereof attached at an end of the body.

14. A method of making a spiral filter for a body lumen, the method comprising:

forming a body from an elongate member having a cylindrical, spiral configuration having loops encircling an axis extending along the length of the body, the body being sized to be implanted into a body lumen to transition from a compressed cylindrical state to a deployed cylindrical state; and forming a first group of a plurality of members positioned around at least one loop of the body at a first position on the axis, the first group of the plurality of members being oriented towards the axis at a first angle, the first group of the plurality of members being arranged to lyse particulates of a selected size; and forming a second group of a plurality of members positioned around at least one loop of the body at a second position on the axis, and radiating towards the axis of the filter at a second angle, the second group of the plurality of members being oriented to inhibit particulates of another selected size from passing through the body, the second group of the plurality of members being dimensioned to allow blood components smaller than the selected size and the another selected size to pass through the body;

where the first angle at which the first group of the plurality of members is oriented toward the axis is different than the second angle at which the second group of the plurality of members radiates toward the axis; and offsetting said members in the first group from said members in the second group by a distance along the length of the body.

15. The method of claim 14, wherein the spiral configuration is formed by rolling the elongate member to form the body having loops encircling the axis extending along the length of the body.

16. The method of claim 15, wherein the elongate member is at least one of a wire, a wire flattened before being formed into a spiral configuration, and a ribbon.

17. The method of claim 14, wherein the spiral configuration is formed by cutting a tube into an elongate member to form a spiral shaped body having loops encircling the axis extending along the length of the body.

18. The method of claim 14, further comprising bending the elongate member at a junction where an aperture meets the body to extend the elongate member in towards the center of the filter on one side of the body, the first group of members including a member formed by cutting an aperture into the body, the aperture being cut into the body along the thickness of the body.

19. The method of claim 18, further comprising forming engaging portions on the body and bending the engaging portions out from the body in a direction opposite to the member, the engaging portions being formed on at least one of the following the same side of the body as the elongate member or a side of the body opposing the side where the elongate member is located.

20. The method of claim 14, where the distance by which the first and second groups are offset is about ⅔ of the total length of the body.

21. The method of claim 14, wherein the first group of members includes at least one member attached to the body and configured to extend at least a portion of the member into the center of the filter.

22. The method of claim 14, wherein the first group of members each have a first end that is attached to the body and a second end configured to extend towards the axis and configured to taper to a point.

23. The method of claim 22, wherein the elongate member includes an extension, the extension being arranged to extend the elongate member out from the body, the taper being attached to the extension and arranged to angle from the extension towards the body.

24. The method of claim 14, wherein the first group of members is cut into an elongate member using apertures to from a continuous line with sections, the sections forming said members.

25. The method of claim 24, wherein the sections are bent towards one side of the elongate section.

26. The method of claim 25, wherein the elongate section is rolled into the spiral configuration and at least one of the sections being arranged to extend inside the filter when the elongate section is rolled or the sections are bent towards the inside of the filter after the body is formed into a spiral configuration.

27. A method of deploying a filter in a body lumen, the method comprising:
longitudinally elongating an implantable lumen filter such that the implantable lumen filter has a reduced dimension, the implantable lumen filter comprising:
a body formed from an elongate member having a cylindrical, spiral configuration having loops encircling an axis extending along the length of the body, the body being sized to be implanted into a body lumen, the body being capable of transitioning from a compressed cylindrical state to a deployed cylindrical state, and
a first group of members arranged around a loop of the body with a first end of each member attached to the body at a first position on the axis and a second end of each member configured to extend towards the axis at a first angle, said the first group of members being arranged to lyse particulates of a selected size; and
a second group of members arranged around a loop of the body with a first end of each member attached to the body at a second position on the axis and a second end of each member configured to extend at a second angle towards the axis, the second group of members being oriented and dimensioned to allow blood components smaller than the selected size to pass between said second group of members; and where the second group of members is offset a distance along the length of the body from the first group of members; and where the first angle at which the first group of members extends toward the axis is different than the second angle at which the second group of members extends towards the axis; and
loading the implantable lumen filter in a delivery system.

28. The method of claim 27, wherein the filter is deployed in the body lumen by at least one of pulling the delivery system away from the filter or pushing the filter out from the delivery system to release the filter to deploy the filter from at least one of the following one end of the delivery system or a middle section of the delivery system.

29. The method of claim 27, wherein, as the filter is deployed, at least one of the following occurs: the filter expands out against the body lumen and said first group of members spring into place or the filter is expanded with a balloon to fit the filter against the body lumen and the first group of members spring into position after the balloon is deflated.

30. The method of claim 27, wherein the body and the first group of members are formed having a different spring property by annealing the filter material in certain locations differently.

31. A method of retrieving a filter in a body lumen, the method comprising:
locating a filter deployed in the body lumen at a deployment site, the filter comprising:
a body formed from an elongate member having a cylindrical, spiral configuration having loops encircling an axis extending along the length of the body, the body being sized to be implanted into a body lumen to transition from a compressed cylindrical state to a deployed cylindrical state,
a first group of members arranged around a loop of the body at a first position on the axis and configured to extend towards the axis at a first angle, said first group of members being arranged to lyse particulates of a selected size; and
a second group of members arranged around a loop of the body at a second position on the axis and configured to extend towards the axis at a second angle, the second group of members being oriented and dimensioned to allow blood components smaller than the selected size to pass between said second group of members;
where the second group of members is offset a distance from the first group of members along the length of the body; and
where the first angle at which the first group of members is oriented toward the axis is different than the second angle at which the second group of members radiates toward the axis;
delivering a retrieving mechanism to the deployment site of the filter in the body lumen;
capturing the filter with the retrieving mechanism; and
retrieving the filter from the body lumen by retracting the retrieving mechanism.

32. The method of claim 31, wherein each member of the first and second groups of members has a first end that is attached to the body and a second end configured to extend towards the axis.

33. The method of claim 32, wherein the filter includes a retrieval portion attached to an end of the filter, a retrieval member of the retrieving mechanism being inserted into the retrieval portion to capture the filter.

34. The method of claim 32, wherein the filter includes a bushing attached to ends of the first group of members on a side opposite the body, the bushing having a tube configuration with a plate extending through the bushing, a retrieval member of the retrieving mechanism being inserted through the bushing and engaging the plate to capture the filter.

35. The method of claim 31, wherein the filter is retrieved using a retrieving mechanism including a tube and a wire, the wire extending through the tube, and a snare attached to the end of the wire.

36. The method of claim 34, wherein the filter includes a hook attached to an end of the filter and wherein at least one of the following occurs: a snare of the retrieving mechanism encircling the hook to capture the filter or the snare of the retrieving mechanism captures the filter by encircling a loop of the filter with the snare.

37. The method of claim 31, wherein the filter is retrieved using a retrieving mechanism including a tube and a wire, the wire extending through the tube, and pushing members placed at the end of the wire and arranged to extend back towards the tube.

38. The method of claim 37, wherein the filter includes a bushing having a hollow core attached to ends of the first group of members on a side opposite the body, the retrieving mechanism being inserted through the hollow core of the bushing to capture the filter.

39. The method of claim 38, wherein the retrieving mechanism is inserted through the bushing, the pushing members springing out past the outer diameter of the bushing after the pushing members extend through the bushing to capture the filter.

40. The method of claim 31, wherein the filter is retrieved using a retrieving mechanism including a tube and a wire, the wire extending through the tube, and pushing members being attached to the end of the tube and arranged to extend away from the tube.

41. The method of claim 40, wherein the filter includes a bushing attached to ends of the first group of members on a side opposite the body, the pushing members of the retrieving mechanism being used to push against the bushing to capture the filter.

42. The method of claim 31, wherein the filter is retrieved using a retrieving mechanism including a tube and a wire, the wire extending through the tube, rear facing pushing members placed at the end of the wire and arranged to extend back towards the tube, and forward facing pushing members being attached to the end of the tube and arranged to extend away from the tube.

43. The method of claim 42, wherein the filter includes a bushing having a hollow core attached to ends of the first group of members on a side opposite the body, the retrieving mechanism being inserted through the hollow core of the bushing, the rear facing pushing members springing out past the outer diameter of the bushing after the rear facing pushing members extend through the bushing, the forward facing pushing members of the retrieving mechanism being used to push against the bushing on a side opposite the rear facing pushing members, the rear facing pushing members and forward facing pushing members being used to lock in the bushing and to capture the filter.

44. The method of claim 31, further comprising:
locating an additional filter deployed in the body lumen at a deployment site, the additional filter comprising:
a body formed from an elongate member into a spiral configuration having loops encircling an axis extending along the length of the body, the body being sized to be implanted into a body lumen, and
a third group of members arranged around a loop of the body and configured to extend at least a portion of each of said members in towards the axis, said third group of members being arranged to lyse particulates of a selected size; and
a fourth group of members arranged around a loop of the body and configured to extend towards the axis, the fourth group of members being oriented and dimensioned to allow blood components smaller than the selected size to pass between said fourth group of members;
delivering a retrieving mechanism to the deployment site of the additional filter in the body lumen;
capturing the additional filter with the retrieving mechanism; and
retrieving the additional filter from the body lumen by retracting the retrieving mechanism.

45. The method of claim 44, wherein the filter is retrieved before the additional filter is retrieved.

* * * * *